United States Patent [19]

Wilkerson et al.

[11] Patent Number: 5,414,004
[45] Date of Patent: May 9, 1995

[54] NEUROTRANSMITTER RELEASERS USEFUL FOR COGNITION ENHANCEMENT

[75] Inventors: Wendell W. Wilkerson, New Castle; Richard A. Earl, Wilmington, both of Del.; Matthew E. Voss, Lincoln University, Pa.

[73] Assignee: The Du Pont Merck Pharmaceutical Company, Wilmington, Del.

[21] Appl. No.: 124,523

[22] Filed: Sep. 20, 1993

Related U.S. Application Data

[63] Continuation of Ser. No. 821,572, Jan. 16, 1992, abandoned.

[51] Int. Cl.$^6$ .............. A61K 31/44; C07D 401/06; C07D 401/14
[52] U.S. Cl. .................. 514/339; 514/333; 546/256; 546/273
[58] Field of Search ............... 546/256, 273; 514/333, 514/339

[56] References Cited

U.S. PATENT DOCUMENTS

| | | | |
|---|---|---|---|
| 4,760,083 | 7/1988 | Myers et al. | 544/296 |
| 5,006,537 | 4/1991 | Effland et al. | 514/339 |

FOREIGN PATENT DOCUMENTS

| | | |
|---|---|---|
| 0311010 | 12/1989 | European Pat. Off. |
| 0415102A1 | 6/1991 | European Pat. Off. |
| 91/01306 | 2/1991 | WIPO |

OTHER PUBLICATIONS

Cook et al., Drug Dev. Res. 1990, 19:301.
Nickolson et al., Drug Dev. Res. 1990, 19:285.
DeNoble et al., Pharm. Biochem. Behav. 1990, 36:957.
Saletu et al., Br. J. Clin. Pharm. 1989, 28:1.
Saletu et al., Chem. Abstracts. 1989, 111:108875p.

*Primary Examiner*—Raymond Henley, III
*Assistant Examiner*—Phyllis G. Spivack
*Attorney, Agent, or Firm*—Gerald J. Boudreaux

[57] ABSTRACT

Compounds of the following formula have been shown to enhance the release of the neurotransmitter acetylcholine, and thus may be useful in the treatment of diseases of man involving learning and cognition, where subnormal levels of this neurochemical are found

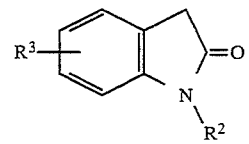

wherein
 $R^1$ is 4-,3-, or 2-pyridyl, 2-fluoro-4-pyridyl or 3-fluoro-4-pyridyl;
 $R^2$ is alkyl of 1 to 10 carbons, cycloalkyl of 3 to 8 carbons, 2-,3-, or 4-pyridyl, Phe or Phe-W;
 Phe is a phenyl group;
 W is F, Cl, Br, $R^4$, —OH, —OR$^4$, —NO$_2$, —NH$_2$, —NHR$^4$, —NR4R$^4$, —CN, —S(O)m —R$^4$;
 $R^3$ is H, F, Cl, Br, —CN, —OH, —NO$_2$, —NH$_2$, —CF$_3$, —NHR$^4$, —NR$^4$R$^4$, R$^4$, —OR$^4$, —S(O)$_m$ —R$^4$
 $R^4$ is alkyl of 1 to 4 carbons, CH$_2$Phe— or Phe—;
 $R^5$ is —(CH$_2$)$_n$—Y or —OCOR$^4$;
 Y is NH$_2$, —NHR$^4$, —NR$^4$R$^4$, —NHCOR$^4$, —NHCO$_2$R$^4$, F, Cl, Br, OR$^4$, —S(O)$_m$R$^4$, —CO$_2$H, —CO$_2$R$^4$, —CN, —CONR$^4$R$^4$, —CON HR$^4$, CONHR$^4$, —CONH$_2$, —COR$^4$; —CH=CH-CO$_2$R$^4$, OCOR$^4$, CO≡CCO$_2$R$^4$, —CH=CHR$^4$, or —C≡CR$^4$;
 m is 0, 1 or 2;
 n is 1 to 7;
and physiologically suitable salts thereof.

51 Claims, No Drawings

NEUROTRANSMITTER RELEASERS USEFUL FOR COGNITION ENHANCEMENT

This is a continuation division of application Ser. No. 07/821,572 filed. Jan. 16, 1992, now abandoned.

BACKGROUND OF THE INVENTION

1. Field of Invention

This invention relates to disubstituted polycyclic compounds, to pharmaceutical compositions thereof, and methods of use in mammals to treat cognitive disorders, neurological dysfunction, and/or mood disturbances such as, but not limited to degenerative nervous system diseases. Additionally, these compounds can be used as reagents in studies on the biochemical mechanism of neurotransmitter based diseases.

2. Background Including Prior Art

Increasingly there is a need for effective treatments for nervous system disorders and neurological deficiencies. Many of these diseases correlate with increasing age due mainly to degenerative changes in the nervous systems. Although in early stages of some diseases, certain systems are rather specifically affected (e.g., cholinergic systems in Alzheimer's Disease and Myasthenia Gravis, the dopaminergic system in Parkinson's Disease, etc.), multiple neurotransmitter system deficiencies (acetylcholine, dopamine, norepinephrine, serotonin) are generally found at later stages of disease such as senile dementia, multi-infarct dementia, Huntington's Disease, mental retardation, etc. This explains the generally observed multiple symptomatology that includes cognitive, neurological, and effective/psychotic components (see Gottfries, Psychopharmacol., 1985, 86, 245). Deficits in the synthesis and release of acetylcholine in the brain are generally thought to be related to cognitive impairment (see Francis, et al., New England J. Med., 1985, 7, 313) whereas neurological deficits (e.g. Parkinsonian symptoms) and mood/mental changes may be related to impairment of dopaminergic and serotonergic systems, respectively. Other neurological deficits (e.g. Myasthenia Gravis) are related to cholinergic deficiencies in the peripheral nervous system.

Treatment strategies employed previously encompass vasoactive drugs like vincamine and pentoxifylline; metabolic enhancers like ergoloid mesylates, piracetam, and naftidrofuryl; neurotransmitter precursors like I-DOPA, choline, and 5-hydroxytryptamine; transmitter metabolizing enzyme inhibitors such as physostigmine; and neuropeptides like adrenocorticotropic hormone and vasopressin-related peptides. Except for I-DOPA treatment for Parkinson's Disease and cholinesterase inhibitor treatment for Myasthenia Gravis, these treatment strategies have generally failed to enhance the residual function of the affected systems by enhancing the stimulus-induced release of neurotransmitters. Theoretically, such an enhancement would improve the signal-to noise ratio during chemical transmission of information, thereby reducing deficits in processes related to cognition, neurological function, and mood regulation.

Cook, L., et al., Drug Development Research 19:301–314 (1990), Nickolson, V. J., et al., Drug Development Research 19:285–300 (1990), and DeNoble, V. J., et al., Pharmacology Biochemistry & Behavior, Vol. 36, pp. 957–961 (1990), all have shown by invitro testing that the drug DuP 996, 3,3-bis(4-pyridinylmethyl)-1-phenylindolin-2-one, is useful in the treatment of cognition dysfunction. Saletu, B., et al., Br. J. Clin. Pharmac. (1989), 28, 1–16, suggest that DuP 996 may exhibit indirect action or may have an active metabolite, and that three metabolites have been identified, a mono-N-oxide, a bis-oxide and a C-dealkylated alcohol. Chem. Abstracts 111(13):108875p suggest that the following structure is one of the above-named metabolites metabolite of DuP 996:

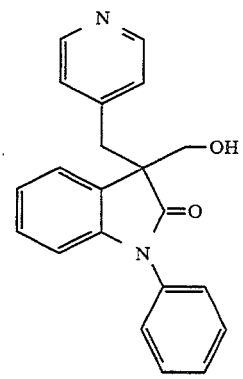

Neither reference presented chemical data to support their hypotheses.

European Patent Application 311,010, published Apr. 12, 1989, discloses that α, α-disubstituted aromatics or heteroaromatics of the formula:

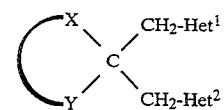

or a salt thereof wherein X and Y are taken together to form a saturated or unsaturated carbocyclic or heterocyclic first ring and the shown carbon in said ring is α to at least one additional aromatic ring or heteroaromatic ring fused to the first ring;

one of $Het^1$ or $Het^2$ is 2, 3, or 4-pyridyl; or 2, 4, or 5-pyrimidinyl, and the other is selected from
(a) 2, 3, or 4-pyridyl
(b) 2, 4, or 5-pyrimidinyl
(c) 2-pyrazinyl
(d) 3 or 4-pyridazinyl,
(e) 3 or 4-pyrazolyl,
(f) 2 or 3-tetrahydrofuranyl, and
(g) 3-thienyl are useful as cognition enhancers. U.S. Pat. No. 4,760,083, issued to Myers et al. on Jul. 26, 1988, discloses that indolines of the following formula are useful for treatment of cognitive deficiencies:

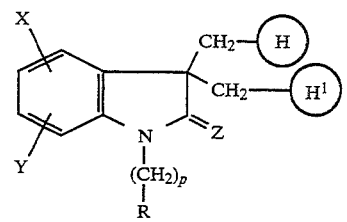

wherein p is 0 or 1; Z is 0 or S; R is C, —$C_{10}$ alkyl, $C_1$-$C_3$ cycloalkyl, 2-pyridyl, 3-pyridyl, 4-pyridyl or

V, W, X and Y are independently halo, C, —C₃ alkyl, OR¹, NO₂, CF₃, CN or NR²R²;

R¹ and R² independently are H or C₁C₃ alkyl;

—H and —H¹ independently are 6-membered heterocyclic aromatic rings containing at least one nitrogen atom as a part of the ring optionally substituted with one substituent selected from the group C₁-C₃ alkyl, halo, OR¹ or NR¹R², or an N-oxide or pharmaceutically suitable acid addition salt thereof. These references claim the necessity of heteroaryl groups for activity. Patent WO 91/01/306, Feb. 7, 1991 discloses oxindole derivatives of formula:

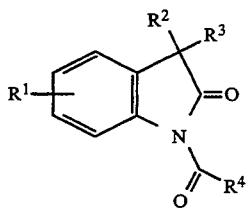

useful for treating senile dementia, i.e. improving brain functions and activating and protecting brain metabolism. In the above formula, R¹ represents hydrogen, halogen, lower alkyl, or lower alkoxy; R²represents hydrogen or lower alkyl; R³ represents —CH₂—R⁵, wherein R⁵ represents alkyl which may be cyclic, benzodioxanyl, or phenyl which may be substituted with a plurality of halogen, lower alkyl, lower alkoxy, hydroxy, diethylamino, trifluoromethyl, nitrile, nitro, or benzyloxy; alternatively R² and R³ may be combined together to form =CH—R⁵, wherein R⁵ is defined above; and R⁴represents 1-propylbutyl, pyridyl, phenyl or substituted phenyl. This reference only discloses imides and does not suggest alkyl or aryl substituted amides.

EP415-102-A discloses a series of 1,3-dihydro-1-(pyridinylamino)-2H-indol-2-ones as having analgesic, anticonvulsant, and/or memory enhancing activity and are useful in the treatment of Alzheimer's disease.

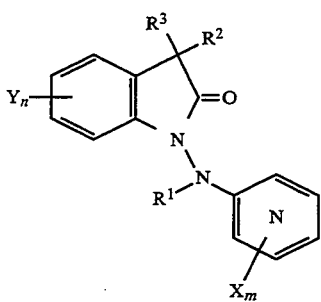

where R¹, R² and R³ are independently hydrogen, loweralkyl, aryl, arylloweralkyl or heteroaryloweralkyl selected from the group consisting of pyridinylmethyl, pyridinylethyl, thienylmethyl, thienylethyl; or R² and R³together form a cycloalkane ring of 4 to 6 carbons or a spiro-fused aryl cycloalkane or heterocycloalkyl selected from the group consisting of piperidine and tetrahydropyran; X and Y are independently hydrogen, halogen, hydroxy, loweralkyl, loweralkoxy, nitro, amino or trifluoromethyl; m and n are independently integers of 1 to 3. This reference disclosed hydrazides and does not suggest alkyl or aryl substituted amides.

SUMMARY OF THE INVENTION

Presently, it has been found that certain polycyclic compounds having "mixed pendent group" gem substitutions enhance the stimulus-induced release of neurotransmitters, specifically acetylcholine in nervous tissue, and thus improve processes involved in learning and memorization of an active avoidance task. Most particularly, according to the present invention there are provided novel compounds of the formula

where Q is

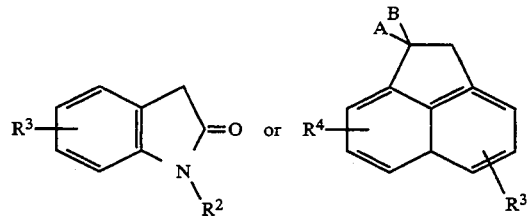

A and B are independently selected from the group including H, R⁴, —OH and—OCOR⁴, or A and B together form =O, =S, =CH₂, =CHR⁴, =C(R⁴), =NOH, =NOR⁴, 1,3-dioxane, 1,3-dioxolane, 1,3-dithiane or 1,3-dithiolane;

R¹ is 4-,3-, or 2-pyridyl, pyrimidyl; pyrazinyl, 2-fluoro-4-pyridyl or 3-fluoro-4-pyridyl;

R² is alkyl of 1 to 10 carbons, cycloalkyl of 3 to 8 carbons, 2-,3-, or 4-pyridyl, Phe or Phe-W;

Phe is a phenyl group;

W is F, Cl, Br, R⁴, —OH, —OR⁴, —NO₂, —NH₂, —NHR⁴, —NR⁴R⁴, —CN, —S(O)$_m$—R⁴;

R³ is H, F, Cl, Br,—CN,—OH,—NO₂, —NH₂,—CF₃, —NHR⁴, —NR⁴R⁴, R⁴, —OR⁴, —S(O)$_m$—R⁴;

R⁴ and R⁴' are alkyl of 1 to 4 carbons, CH₂Phe—W or Phe—W;

R⁵ is —(CH₂)$_n$—Y or —OCOR⁴;

Y is H, OH, NH₂, —NHR⁴, —NR⁴R⁴, —NHCOR⁴, —NHCO₂R⁴, F, Cl, Br, OR⁴, —S(O)$_m$R⁴, —CO₂H, —CO₂R⁴, —CN, —CONR⁴R⁴, —CONHR⁴, —CONH₂, —COR⁴; —CH=CH-CO₂R⁴, OCOR⁴, Phe, Phe-W, -C≡CCO₂R⁴, —CH=CHR⁴, or —C≡CR⁴;

m is 0, 1 or 2;

n is 1 to 7;

provided that, when Q is oxindole and R⁵ is (CH₂)$_n$ Y, then Y is other than OH;

and physiologically suitable salts thereof.

This invention also relates to pharmaceutical compositions comprising a suitable pharmaceutical carrier and an amount of one or more of the above-described compounds effective to treat cognitive or neurological dysfunction. Still further, this invention relates to a method of treating cognitive or neurological dysfunction in a mammal comprising administering to the mammal a therapeutically effective amount of one or more of the above-described compounds.

DETAILED DESCRIPTION OF THE INVENTION

Preferred Embodiments

Preferred compounds of this invention are those of Formula I wherein, together or independently:

A and B together form =O;
$R^1$ is (a)4-pyridyl, (b)4-pyrimidyl, or (c) 2-fluoro-4-pyridyl;
$R^5$ is $-(CH_2)_n-Y$;
n is 1 to 5;
Y is H, $-OH$, $NH_2$, $NHR^4$, $NR^4R^4$, F, Cl, Br, $-CO_2H$, $-CO_2R^4$, $-CN$, $-CONHR^4$, $-CONH_2$, $-CONR^4R^4$, $-COR^4$, $-=CH-CO_2R^4$, $-OCOR^4$, or -Phe-W
W is F, Cl, or Br; $R^4$, $-OR^4$, $-S(O)_m-R^4$, $-CN$, $-NO_2$, or $-NH_2$;
$R^4$ is alkyl of 1 to 4 carbons, and m is 0, 1, 2.

More preferred compounds of Formula I are those where, together or independently:

$R^1$ is (a)4-pyridyl, (b) 4-pyrimidyl, or (c) 2- fluoro-4-pyridyl;
$R^5$ is $-(CH_2)_n-Y$;
n is 1 to 4;
Y is $-CO_2R^4$, $-CN$, $-CONHR^4$, $-CH=CH-CO_2R^4$, $-OCOR^4$,
$R^2$ is 4-pyridyl, Phe or Phe-W,
W is F, Cl, or Br; $NO_2$, CN, or $CH_3$;
$R^3$ is H, F, Cl, or Br; and
$R^4$ is alkyl of 1 to 2 carbons.

Specifically preferred compounds of Formula I are:
(a) 2,3-Dihydro-2-oxo-1-phenyl-3-(4-pyridinylmethyl)-1H-indole-3-butanoic acid ethyl ester Hydrochloride;
(b) (+)-2,3-Dihydro-2-oxo-1-phenyl-3-(4-pyridinylmethyl)-1H-indole-3-butanoic acid ethyl ester Hydrochloride;
(c) 2,3-Dihydro-2-oxo-1-phenyl-3-(4-pyridinylmethyl)-1H-indole-3-pentanenitrile Hydrochloride;
(d) 1,3-Dihydro-3-[(3-cyanophenyl)methyl]-1-phenyl-3-(4-pyridinylmethyl)-2H-indol-2-one Hydrochloride;
(e) 2,3-Dihydro-2-oxo-1-phenyl-3-(4-pyridinylmethyl)-1H-indole-3-butanenitrile Hydrochloride;
(f) 2,3-Dihydro-2-oxo-1-phenyl-3-(4-pyridinylmethyl)-1H-indole-3-hexanenitrile Hydrochloride;
(g) 1,3-Dihydro-3-(4-hydroxybutyl)-1-phenyl-3-(4-pyridinylmethyl)-2H-indol-2-one Hydrochloride;
(h) 1,3-Dihydro-1-phenyl-3-(phenylmethyl)-3-(4-pyridinylmethyl)-2H-indole-2-one Hydrochloride It should be recognized that the above-identified groups of compounds are preferred embodiments of this invention, but that their description herein is in no way intended to limit the overall scope of this invention.

Synthesis

Many of the compounds of this invention can be synthesized by the sequence shown in Schemes 1a and 1b, or by modifications thereof obvious to one skilled in the art. Generally, compound $R^1-CH_2-Q-H$ is treated with a base, in an appropriate aprotic solvent and temperature, to generate an anion ($R^1-CH_2-Q$:). The resulting anion is then alkylated with an appropriate alkyl halide ($R^5$-Hal) to give the desired compounds ($R^1-CH_2-Q-R^5$).

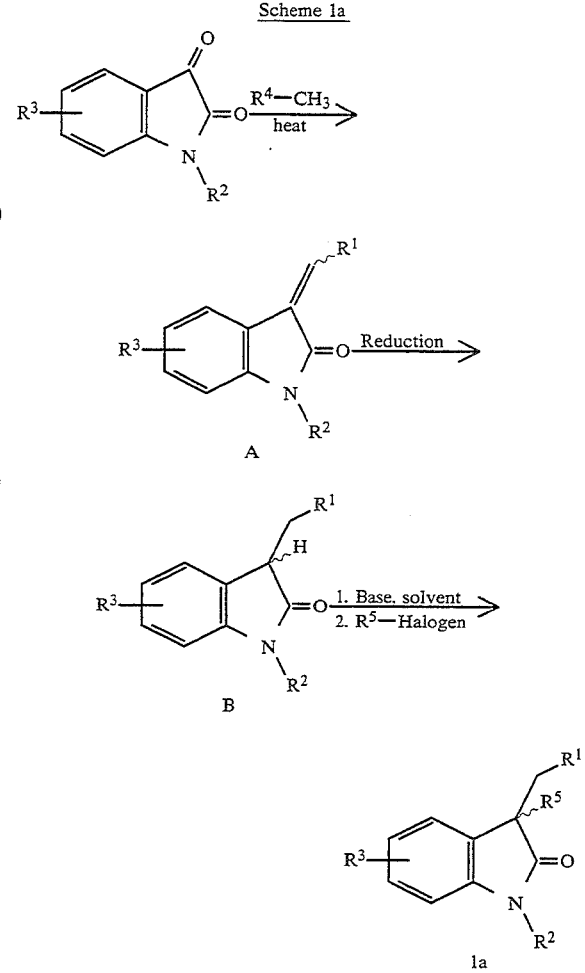

Scheme 1a

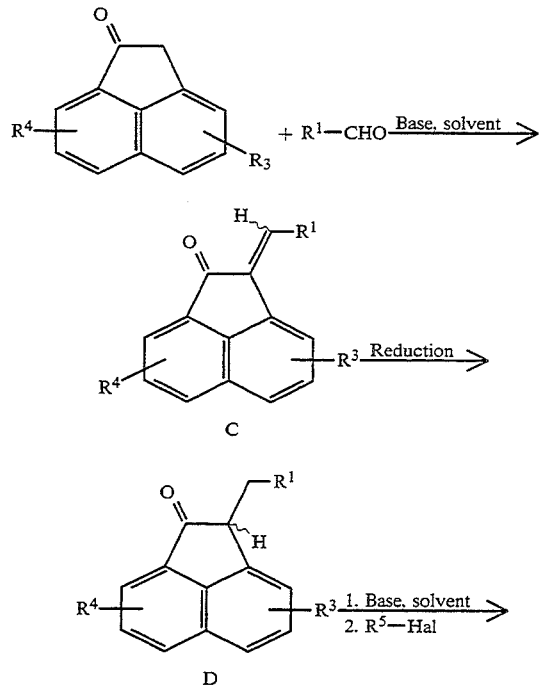

Scheme 1b

-continued
Scheme 1b

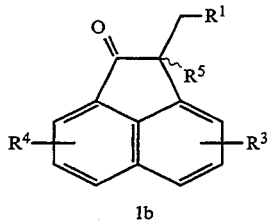

1b

Suitable bases for forming the anion include, but are not limited to, sodamide, lithium diisopropylamide (LDA), sodium hydride, potassium tert-butoxide, sodium alkoxide, potassium alkoxide, potassium hydride, lithium 2, 2, 6, 6- tetramethylpiperidine, butyl lithium, sec-butyl lithium, tert- butyl lithium, and lithium- sodium-, or potassium hexamethyldisilazide. The reaction can be conducted in an aprotic solvent, generally in an ether, such as but not limited to, tetrahydrofuran (THF), dioxane, glyme, diglyme, or diethyl ether. Additionally, the reaction can be run in dimethylformamide or dimethylacetamide. However, if Q is soluble in a nonpolar solvent, the reaction can be carried out in a hydrocarbon solvent such as hexanes, heptane, cyclohexane, methylcyclohexane, benzene or toluene. Depending on the strength of the base, the reactions can be conducted at a temperature from about −78° C. to solvent reflux temperature.

Typically, a 3-(4-pyridinylmethyl)-oxindole or 2-(4-pyridinylmethyl)acenaphtheone is dissolved or suspended in dry THF, cooled to 0° C., treated with 1.1 equivalents of sodium hydride, stirred for 30 to 60 minutes under an inert gaseous environment, and treated dropwise with a solution of the alkylating agent. The reaction is stirred in the cold for one hour, and at ambient temperature until no starting material can be detected by chromatographic methods. The reaction mixture is concentrated at reduced pressure, and the residue is partitioned between water and methylene chloride. The organic phase is washed with water and brine, dried over anhydrous magnesium sulfate, filtered, and concentrated at reduced pressure. Depending on the purity, the compounds of this invention may be collected as an oil, gum, or amorphous solid; or recrystallized from an appropriate solvent system; or further purified by chromatographic, sublimation, or distillation processes. The compounds may also exist as the "free base" or as an acid addition salt formed from pharmaceutically acceptable acids. Additionally, compounds of Formula I may exist as racemates, diastereomeric mixtures, or their optically pure isomers.

Other representative compounds of this invention can be synthesized by converting one $R^5$ Y-group to another, as in the case of an ester (Y=CO$_2$R$^4$) being converted to the corresponding alcohol (Y=OH) which can be further converted to an ether (Y=OR$^4$) or the "reverse ester" (Y=O—COR$^4$). For such a case, the ester can be saponified to give the acid (Y =CO$_2$H) which can be reduced to the alcohol. Alternatively, the ester can be directly reduced to the alcohol. An alternative approach to the "reverse ester" compounds [Y=—OC(=O)R$^4$], can be initiated with the ester, which can be reduced to the alcohol, which can be subsequently acylated with an acid halide or anhydride, or by coupling the alcohol to an acid using dicyclohexylcarbodiimide, carbonyl diimidazole, or some other coupling agent.

A nitrile can be oxidized to the corresponding amide using the procedure described by Noller, Org. Syn. Coll. Vol. II, p 586. The same amide can be prepared from the corresponding ester by saponification, activation of carboxyl, and reaction with ammonia or ammonia derivatives. By substituting primary or secondary amines for ammonia, other compounds of this invention may be prepared.

Intermediate R$^1$—CH$_2$—Q: can be reacted with a di-haloalkane to give the alkylhalide (Y=Hal) which can be reacted with a :OR$^4$ to give the corresponding ether, or with a thiol to give the thioether. The thioether can be selectively oxidized to the sulfoxide (m=1) or the sulfone (m=2).

The compounds of the invention and their synthesis are further illustrated by the following examples and preparations. All temperatures are in degrees Celsius.

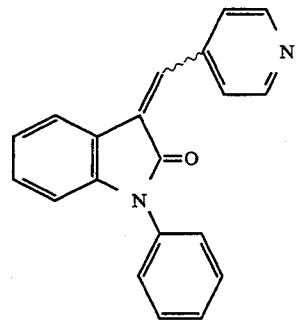

1,3-Dihydro-3-(4-pyridinylmethylene)-1-phenyl-2H-indole-2-one

The compound was prepared as described by Bryant and Huhn, U.S. Pat. No. 4,806,651.

Preparation 2

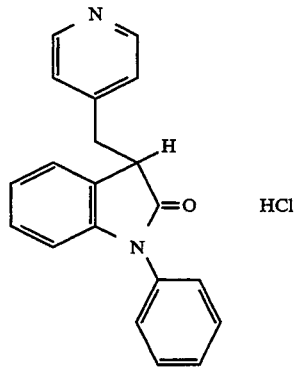

1,3-Dihydro-1-phenyl-3-(4-pyridinylmethyl)-2H-indol-2-one Hydrochloride

A solution of 1,3-dihydro-3-(4-pyridinylmethylene)-1-phenyl-2H-indole-2-one (7.46 g, 25 mmol) in 100 ml THF was treated with NaBH$_4$ (1.0 g, 26.4 mmol) and stirred at room temperature for 24 h, and refluxed for 2 h. The mixture was cooled to room temperature and treated with 75 ml acetic acid. The mixture was concentrated in vacuo, and the residue was made alkaline with 1N NaOH and extracted with 200 ml CH$_2$Cl$_2$. The extract was washed with water and brine, dried over anhydrous MgSO$_4$, filtered, and concentrated to a thick oil that crystallized on sitting at room temperature overnight. The desired product was obtained in 72% (6.14 g) yield; mp 137°-140° C.; IR(nujol): C=O @1703 cm$^{-1}$; NMR(DMSOd$_6$TMS): δ3.61 (m, 2H, CH$_2$-Pyr), 4.39 (t, 1H, CH—C-Pyr), [6.66 (d, 1H), 7.07 (dd, 1H), 7.22 (dd, 1H), 7.34 (m, 3H), 7.45 (m, 1H), 7.56 (m, 2H), Phe+1,2-Phe], [7.91 (d, 2H), 8.82 (d, 2H, 4-Pyr], mass spec m/e 301 (M+1).

EXAMPLE 1

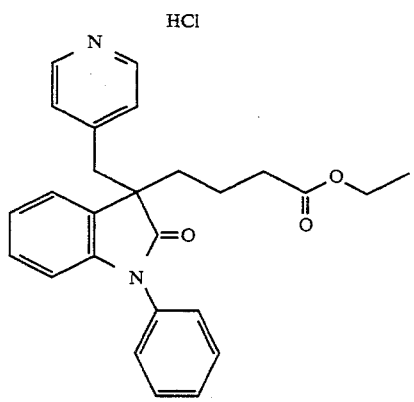

2,3-Dihydro-2-oxo-1-phenyl-3-(4-pyridinylmethyl)-1H-indole-3-butanoic acid ethyl ester Hydrochloride A solution of 1,3-dihydro-1-phenyl-3-(4-pyridinylmethyl)-2H-indol-2-one hydrochloride (33.7 g, 0.1 mol) in 200 ml CH$_2$Cl$_2$ was treated with 150 ml 1N NaOH. The organic phase was washed with water and brine, dried over anhydrous MgSO$_4$, filtered, and concentrated to an oil which solidified on cooling. The "free base" was dissolved in 150 ml dry THF, cooled in an ice bath, treated with NaH (2.88 g, 0.12 mol), and stirred under dry nitrogen for 30 min. The mixture was treated with ethyl 4-bromobutyrate (19.5 g, 0.1 mol) in 25 ml dry THF. The mixture was stirred in the ice for 1 h and 16 h at room temperature. The reaction mixture was concentrated in vacuo, and the residue was partitioned between 300 ml Et$_2$O and 200 ml water. The organic phase was washed with water and brine, dried over anhydrous MgSO$_4$, filtered, treated with 150 ml 1N HCl-Et$_2$O, and concentrated in vacuo. The residue was dissolved in 100 ml anhydrous EtOH with warming and stirred at room temperature for 24 h. The resulting crystals were collected by filtration, washed with a small portion of cold EtOH and Et$_2$O, and dried in vacuo at 80° C. to give the desired product in 86% (38.6 g) yield; mp 182.5°-183.0° C.; IR(nujol): C=O @1722 and 1703 cm$^{-1}$; NMR(DMSOd$_6$ TMS: δ1.15 (t, 3H, CH$_3$), 1.2, 1.3 (2m, 2H, CH$_2$CCCO), 2.1 (m, 2H, CH$_2$CCO), 2.26 (t, 2H, CH$_2$CO), [3.43 (d, 1H, J12), 3.64 (d, 1H, J12) CH$_2$-Pyr], 4.02 (q 2H, OCH$_2$), [6.54 (m, 1H), 7.2 (m, 2H), 7.5 (m, 5H), 7.68 (m, 1H) Ar—N-Phe], [7.10 (d, 2H), 8.70 (d, 2H) 4-Pyr]; Anal calcd for C$_{26}$H$_{26}$N$_2$O$_3$ HCl, MW 450.97: C, 69.25; H, 6.04; N, 6.21. Found: C, 69.02; H, 5.98; N, 6.52. Mass spec m/e 415(M+1-HCl).

EXAMPLE 2

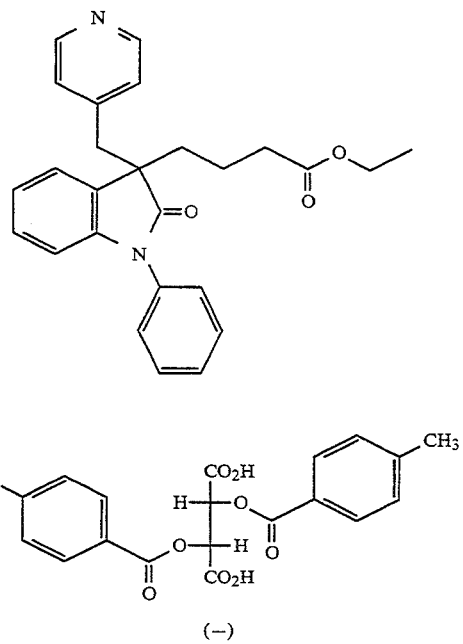

2,3-Dihydro-2-oxo-1-phenyl-3-(4-pyridinylmethyl)-1H-indole- 3-butanoic acid ethyl ester (-)-2,3-bis(4-Methylbenzoyloxy)butanedioate 2,3-Dihydro-2-oxo-1-phenyl-3-(4-pyridinylmethyl)-1H-indole-3-butanoic ethyl ester hydrochloride (19.33 g, 0.043 mol) was partitioned between 200 ml Et$_2$O and 200 ml water containing NaHCO$_3$ (4.0 g, 0.048 mol). The organic layer was washed with water and brine, dried over anhydrous MgSO$_4$, filtered, and concentrated in vacuo. The residue was dissolved in EtOH (100 g) and treated with O,O-(-)-p-toluyl-L-tartaric acid monohydrate (17.33 g, 0.043 mol). The mixture was warmed at 60° C. to effect solution, and the mixture was stirred at room temperature for 24 h. The resulting crystals were collected by filtration, washed with 3×50 ml cold EtOH and 2×50 ml Et$_2$O, and dried in vacuo to give the product in 24.5% (8.6 g) overall yield which implies 48.9% of one isomer; mp 135.0°-136.0° C. dec.; IR(KBr): 1725 and 1711 cm$^{-1}$; NMR(CDCl$_3$ TMS): δ1.21 (t, 3H, CH$_3$), 1.38 (m, 2H, CH$_2$CCCO), 2.0-2.3 (m, 4H, CH$_2$CH$_2$CO), 2.35 (s, 6H, 2CH$_3$), [3.08 (d, 1H, J12), 3.30 (d, 1H, J12.) CH$_2$-Pyr], 4.08 (g, 2H, OCH$_2$), 5.92 (s, 2H, 2CH—CO), [6.4 (m, 1H), 6.85 (m, 2H), 7.1 (m, 2H), 7.3(m, 2H), 7.38 (dd, 1H), Ar—N-Phe], [6.93 (d, 2H), 8.27 (d, 2H) 4-Pyr], [7.15 (d, 4H), 7.95 (d, 4H) 4-Me-Phe]; Anal calcd for C$_{26}$H$_{26}$N$_2$O$_3$C$_{20}$H$_{18}$O$_8$, MW 800.87: C, 68.99; H, 5.54; N, 3.50. Found: C, 68.94; H, 5.50; N, 3.56. Mass spec m/e 415(M+1- C$_{20}$H$_{18}$O$_8$), [α]$^{25}$D −61.88° (c,0.6,EtOH).

EXAMPLE 3

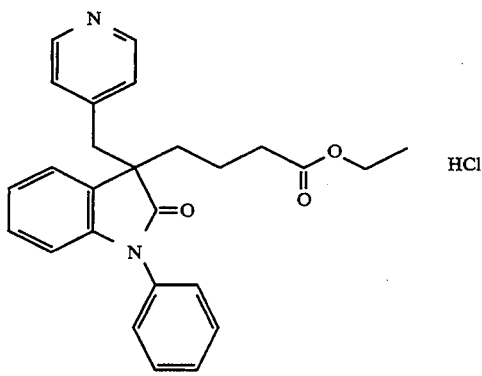

(+)-2,3-Dihydro-2-oxo-1-phenyl-3-(4-pyridinylmethyl)-1H-indole-3-butanoic acid ethyl ester Hydrochloride The salt 2,3-dihydro-2-oxo-1-phenyl-3-(4-pyridinylmethyl)-1H-indole-3-butanoic acid ethyl ester (−)-2,3-bis-(4-methylbenzoyloxy)butanedioate (7.56 g, 0.0094 mol) was partitioned between 100 ml Et$_2$O and 100 ml 5% NaHCO$_3$. The organic layer was washed with water and brine, dried over MgSO$_4$, filtered, treated with 15 ml 1N HCl-Et$_2$O, and concentrated in vacuo to a foam: 4.34 g (100%), NMR(DMSOd$_6$ TMS): δ1.15 (t, 3H, CH$_3$), 1.2, 1.3 (2m, 2H, CH$_2$CCCO) 2.1 (m, 2H, CH$_2$CCO), 2.26 (m, 2H, CH$_2$CO), [3.43 (d, 1H, J$_{12}$), 3.6 (d, 1H, J$_{12}$) CH$_2$-Pyr], 4.02 (q, 2H, OCH$_2$), [6.5 (m, 1H), 7.2 (m, 2H), 7.5 (m, 5H), 7.67 (m, 1H) Ar—N-Phe], [7.18 (d, 2H), 8.70 (d, 2H) 4-Pyr]; Anal calcd for C$_{26}$H$_{26}$N$_2$O$_3$ HCl, MW 450.97: C, 69.25; H, 6.04; N, 6.21. Found: C, 68.94; H, 5.80; N, 6.03. Mass spec m/e 415(M+1 -HCl), [α]$^{25}$D+5.43° (c, 0.6, EtOH), analytical chiral HPLC isomer ratio: 98.2%(+): 1.8%(−).

EXAMPLE 4

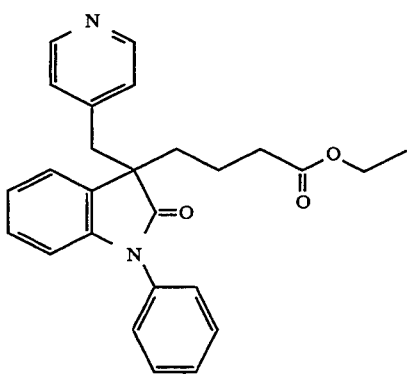

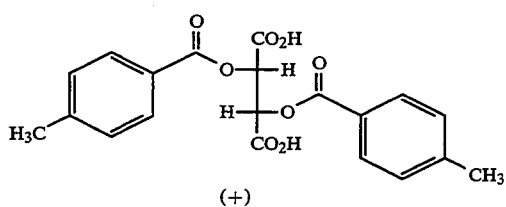

2,3-Dihydro-2-oxo-1-phenyl-3-(4-pyridinylmethyl)-1H-indole- 3-butanoic acid ethyl ester (+)-2,3-bis(4-Methyl-benzoyloxy)butanedioate By substituting O,O-(+)-p-toluyl-D-tartaric acid monohydrate in Example 2, the desired compound was obtained in 56% (12.5 g) yield; mp 132.0°-132.5° C.; NMR(CDCl$_3$ TMS): δ1.21 (t, 3H, CH$_3$), 1.4 (m, 2H, CH$_2$CCCO), 2.0-2.3 (m, 4H, CH$_2$CH$_2$CO), 2.34 (s, 6H, 2CH$_3$), [3.08 (d, 1H, J2), 3.30 (d, 1H, J12)CH$_2$-Pyr], 4.08 (q, 2H, OCH$_2$), [6.4 (m, 1H), 6.85 (m, 2H), 7.1 (m, 2H), 7.3 (m, 4H) Ar-N-Phe], [6.93 (d, 2H), 8.27 (d, 2H) 4-Pyr], [7.35 (d, 4H), 7.95 (d, 4H) 1,4-Phe]; Anal calcd for C$_{26}$H$_{26}$N$_2$O$_3$ C$_{20}$H$_{18}$O$_8$, MW 800.87: C, 68.99;H, 5.54; N, 3.50. Found: C, 69.13; H, 5.55; N, 3.61. Mass spec m/e 415(M+1), [α]$^{25}$D+61.44° (c, 0.6, EtOH).

EXAMPLE 5

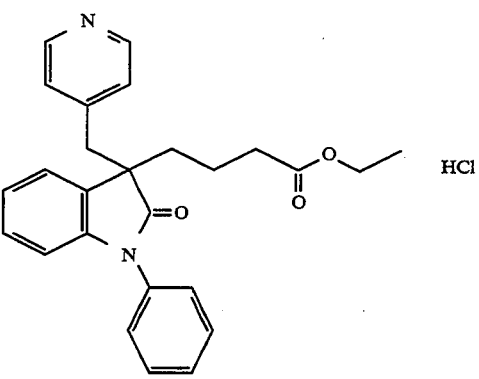

(−)-2,3-Dihydro-2-oxo-1-phenyl-3-(4-pyridinylmethyl)-1H-indole-3-butanoic acid ethyl ester Dihydrochloride By substituting 2,3-Dihydro-2-oxo-1-phenyl-3-(4-pyridinylmethyl)-1H-indole-3-butanoic acid ethyl ester (+)-2,3-bis(4-Methylbenzoyloxy)butanedioate in Example 3, the desired product was obtained as a foam in 94% (5.3 g);NMR(DMSOd$_6$TMS): α 1.15 (t, 3H, CH$_3$), 1.2, 1.3 (2m, 2H, CH$_2$CCCO), 2.1 (m, 2H, CH$_2$CCO), 2.27 (t, 2H, CH$_2$CO), [3.46 (d, 1H, J12), 3.68 (d, 1H, J12)CH$_2$-Pyr], 4.04 (q, 2H, OCH$_2$), [6.55 (m, 1H), 7.2 (m, 2H), 7.47 (m, 1H), 7.55 (m, 4H), 7.7 (m, 1H) Ar-N-Phe], [7.13 (d, 2H) 8.75 (d, 2H) 4-Pyr]; Anal calcd for C$_{26}$H$_{26}$N$_2$O$_3$ HCl, MW 450.97: C, 69.25; H, 6.04; N, 6.21. Found: C, 69.25; H, 5.75; N, 6.21. Mass spec m/e 415(M+1); [α]$^{25}$D-5.96° (c, 0.6, EtOH).

EXAMPLE 6

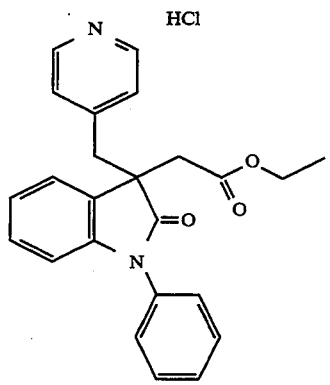

2,3-Dihydro-2-oxo-1-phenyl-3-(4-pyridinylmethyl)-1H-indole-3-acetic acid ethyl ester Hydrochloride By substituting ethyl 2-bromoacetate In Example 1, the desired product was obtained in 66% yield; mp 170°–173° C.

EXAMPLE 7

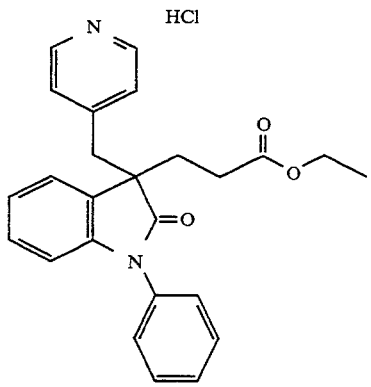

2,3-Dihydro-2-oxo-1-phenyl-3-(4-pyridinylmethyl)-1H-indole-3-propianoic acid ethyl ester Hydrochloride By substituting ethyl 3-bromopropionate In Example 1, the desired product was obtained in 94% yield; mp 181°–182° C.

EXAMPLE 8

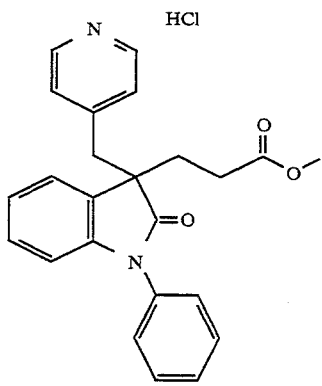

2,3-Dihydro-2-oxo-1-phenyl-3-(4-pyridinylmethyl)-1H-indole-3-propionoic acid methyl ester Hydrochloride By substituting methyl 3-bromopropionate In Example 1, the desired product was obtained in 76% yield; mp 197°–198° C.

EXAMPLE 9

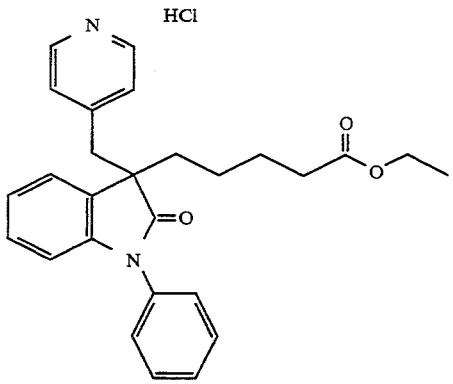

2,3-Dihydro-2-oxo-1-phenyl-3-(4-pyridinylmethyl)-1H-indole-3-pentanoic acid ethyl ester Hydrochloride By substituting ethyl 5-bromovalerate In Example 1, the desired product was obtained in 83% yield; mp 172°–174° C.

EXAMPLE 10

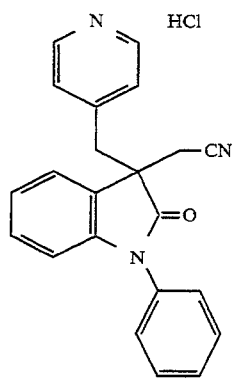

2,3-Dihydro-2-oxo-1-phenyl-3-(4-pyridinylmethyl)-1H-indole-3-acetonitrile Hydrochloride By substituting 2-bromoacetonitrile In Example 1, the desired product was obtained in 82% yield; mp 221° C. dec.

EXAMPLE 11

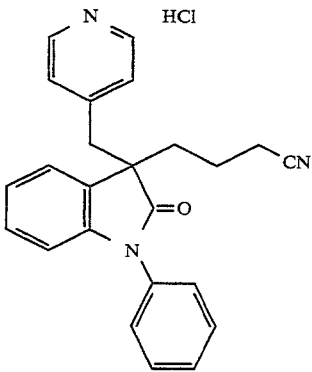

2,3-Dihydro-2-oxo-1-phenyl-3-(4-pyridinylmethyl)-1H-indole-3-butanenitrile Hydrochloride By substituting 4-brombutyronitrile In Example 1, the desired product was obtained in 41% yield; mp 185°–187° C. dec.

EXAMPLE 12

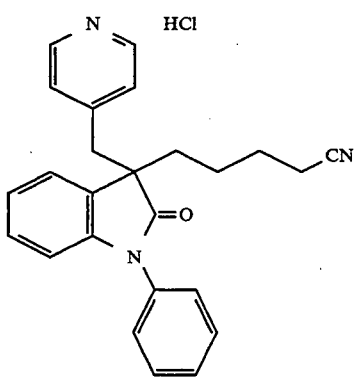

2,3-Dihydro-2-oxo-1-phenyl-3-(4-pyridinylmethyl)-1H-indole-3-pentanenitrile Hydrochloride By substituting 5-bromovaleronitrile In Example 1, the desired product was obtained in 93% yield; mp 164°-165° C. dec.

EXAMPLE 13

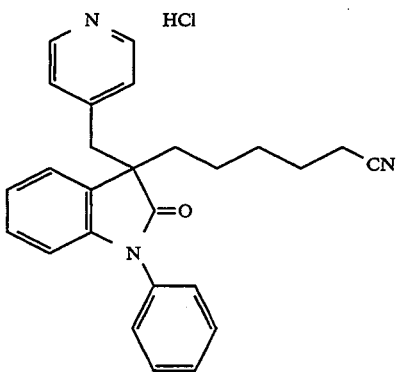

2,3-Dihydro-2-oxo-1-phenyl-3-(4-pyridinylmethyl)-1H-indole-3-hexanenitrile Hydrochloride By substituting 6-bromocapronitrile In Example 1, the desired product was obtained in 42% yield; mp 191°-193° C. dec.

EXAMPLE 14

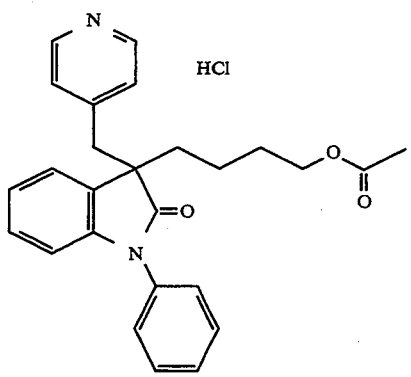

2,3-Dihydro-2-oxo-1-phenyl-3-(4-pyridinylmethyl)-1H-indole-3-butanol acetate ester Hydrochloride By substituting 4-bromobutyl acetate in Example 1, the desired product was obtained in 87% yield; mp 170°-172° C. dec.

Preparation 3

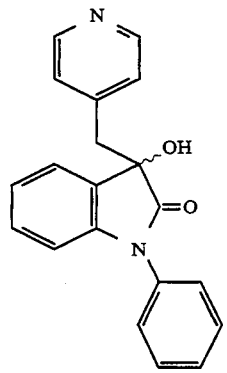

1,3-Dihydro-3-hydroxy-1-phenyl-3-(4-pyridinylmethyl)-2H-indol-2-one

When the anion of 1,3-dihydro-1-phenyl-3-(4-pyridinylmethyl)-2H-iodol-2-one (Preparation 2) was formed in THF with NaH, and dry air was bubbled into the reaction mixture, larger quantities of the alcohol were formed: mp 201°-202° C.; IR(nujol): OH @3170, C=O @1728 cm$^{-1}$; NMR(CDCl$_3$ TMS): δ,3.34 (dd, 2H, CH$_2$-Pyr), 4.34 (broad s, 1H, OH), [6.54 (d, 1H), 6.95 (d, 2H), 7.1 (m, 4H), Phe+1,2-Phe], [6.87 (d, 2H), 8.30 (d, 2H), 4-Pyr]; mass spec m/e 317(M+1); Anal calcd for C$_{20}$H$_{16}$NO$_2$, MW 316.36: C, 75.93; H, 5.10; N, 8.86. Found: C, 76.12; H, 5.01; N, 8.76.

EXAMPLE 15

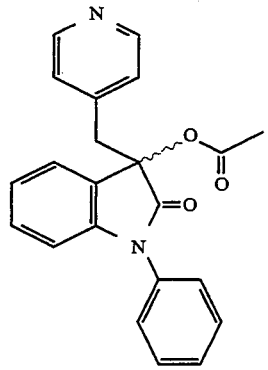

1,3-Dihydro-3-hydroxy-1-phenyl-3-(4-pyridinylmethyl)-2H-indol-2-one Acetate Ester A solution of the alcohol in Preparation 3(0.5 g, 1.58 mmol) in 20 ml CH$_2$Cl$_2$ and 5 ml dry pyridine was treated with excess acetic anhydride and stirred at room temperature for 24 hours. The red solution was poured into 200 ml cold water and extracted with 100 ml CH$_2$Cl$_2$. The organic phase was washed with additional water and brine, dried over MgSO$_4$, filtered, and concentrated in vacuo to give the desired acetate as a yellow solid in 88% (0.5 g) yield; mp 193°-195° C.; IR(nujol): C=O @ 1732 cm$^{-1}$; NMR(CDCl$_3$ TMS): δ2.15 (s, 3H, CH$_3$), 3.3-3.45 (m, 2H, CH$_2$-Pyr), [6.5 (m, 1H), 7.1 (m, 3H), 7.2 (m, 2H), 7.4 (m, 3H), Phe+1,2-Phe],

EXAMPLE 16

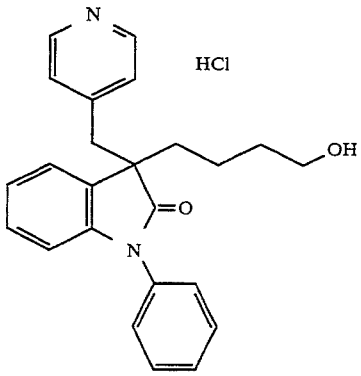

1,3-Dihydro-3-(4-hydroxybutyl)-1-phenyl-3-(4-pyridinylmethyl)-2H-indol-2-one Hydrochloride A suspension of 2,3-Dihydro-2-oxo-1-phenyl-3-(4-pyridinylmethyl)-1H-indole-3-butanoic acid ethyl ester hydrochloride (10.0 g, 22.2 mmol) in 50 ml dry THF was treated with excess 1M BH$_3$-THF and stirred at room temperature for 3 days. The excess borane was decomposed with MeOH, and the mixture was concentrated in vacuo. The residue was digested with 100 ml 1N HCl for 3 hours at 80° C. , and the solution was concentrated. The residue was partitioned between 200 ml EtOAc and 100 ml 5% NaHCO$_3$. The organic phase was washed with water and brine, dried over MgSO$_4$, filtered, treated with 44 ml 1N HCl-Et$_2$O, evaporated in vacuo. The residue was suspended in hot CH$_3$CN and left standing overnight. The resulting crystals were collected by filtration, washed with Et$_2$O, and dried to give the product in 30% (2.72 g) yield; mp 196°–197° C.; IR(nujol): OH @3356 cm$^{-1}$; C=O @1709 cm$^{-1}$; NMR(CDCl$_3$ TMS): δ1.13, 1.24 (2m, 2H, CH$_2$—C—CO), 2.51 (m, 2H, CH$_2$—CO), 2.1–3.0 (m, 2H, CH$_2$—C—C—CO), [3.40 (d, 1H, J=12.4 Hz), 3.54 (d, 1H, J=12.5 Hz), CH$_2$-Pyr], 3.48 (t, 2H, OCH$_2$), [6.5 (m, 1H), 7.2 (m, 2H), 7.4 (m, 6H), Phe+1,2-Phe], [6.99 (d, 2H), 8.49 (d, 2H), 4-Pyr]; mass spec m/e 373(M+1); Anal calcd for C$_{24}$H$_{24}$N$_2$O$_2$ HCl, MW 408.93: C, 70.49; H, 6.16; N, 6.85. Found: C, 70.44; H, 6.00; N, 6.67.

EXAMPLE 17

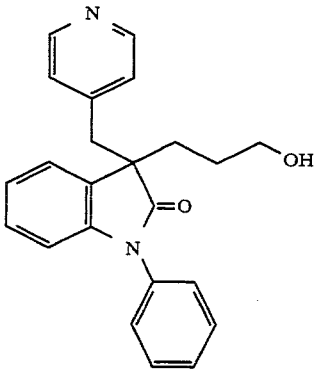

1,3-Dihydro-3-(3-hydroxypropyl)-1-phenyl-3-(4-pyridinyl-methyl)-2H-indol-2-one

By substituting the ester of Examples 7 or 8 in Example 16, the desired alcohol can be prepared in 50–70% yield; mp 146°–147° C.

EXAMPLE 18

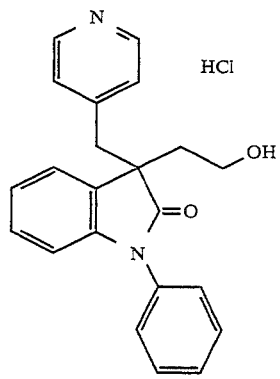

1,3-Dihydro-3-(3-hydroxypropyl)-1-phenyl-3-(4-pyridinyl-methyl)-2H-indol-2-one

By substituting the ester of Example 6 in Example 16, the desired alcohol was obtained in 55% yield; mp 193° C. , dec.

EXAMPLE 19

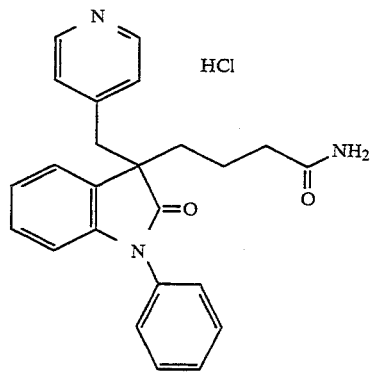

2,3-Dihydro-2-oxo-1-phenyl-3-(4-pyridinylmethyl)-1H-indene-3-butanamide Hydrochloride.

By substituting the product from Example 10 in the method reported by C. M. Noiler, Org. Syn. Coil. Vol. II, Blatt (ed), John Wiley & Sons, New York, 1943, p 586, the desired product was obtained in 72% (3.0 g) yield; mp 232° C. , dec.; IR(nujol): NH @3340, 3300; C=O @1711, 1672 cm$^{-1}$; NMR(DMSO$_6$ TMS): δ1.2 (m, 2H, CH$_2$CCO), 2.0 (m, 4H, CH$_2$—C—CH$_2$CO), 3.4–3.6 (m, 2H, CH$_2$-Pyr), [6.55 (m, 1H), 7.2 (m, 2H), 7.5 (m 5H), 7.65 (m, 1H), Phe+1,2-Phe], 6.73, 7.30 (2 s, 2H, NH$_2$), [7.11 (d, 2H), 8.79 (d, 2H), 4-Pyr]; mass spec m/e 386(M+1).

EXAMPLE 20

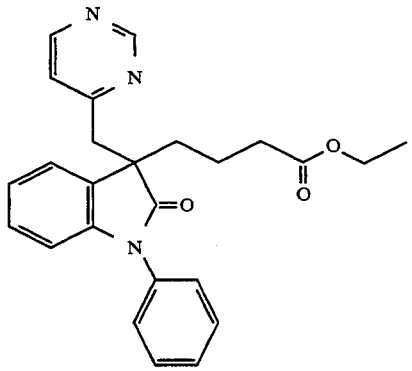

2,3-Dihydro-2-oxo-1-phenyl-3-(4-pyrimidinylmethyl)-1H-indole-3-butanoic acid ethyl ester By substituting 2,3-dihydro-2-oxo-1-phenyl-3-(4-pyrimidinylmethyl)-1H-one and ethyl 4-bromobutyrate in Example 1, the desired product was obtained in 55% yield as an oil; NMR(CDCl₃ TMS) δ1.22 (t, 3H, J=7 Hz); 1.42 (m, 1H); 1.53 (m, 1H) δ2.06 (m, 1H); 2.25 (m, 3H); 3.25 (d, 1H, J=14 Hz); 3.55 (d, 1H, J=14 Hz); 4.09 (q, 2H, J=7 Hz); 6.63 (d, 1J=8 Hz); 6.98 (m, 1H); 7.07 (m, 2H); 7.26 (m, 3H); 7.40 (m, 1H); 7.50 (m, 2H); 8.42 (d, 1H, J=5 Hz); 8.90 (s, 1H). IR(KBr): 1728, 1583, 1501, 1481, 1466, 1376, 1326, 1182, 1157, 758, 700 cm⁻¹; mass spec m/e 416 (M+1); high resolution mass spec m/e calcd 416.197417, m/e found 416.196591 (M+H).

EXAMPLE 21

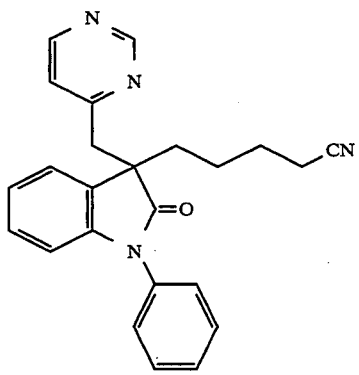

2,3-Dihydro-2-oxo-1-phenyl-3-(4-pyrimidinylmethyl)-1H-indole-3-pentanenitrile

By substituting 2,3-Dihydro-2-oxo-1-phenyl-3-(4-pyrimidinylmethyl)1H-indole and 5-bromopentanenitrile in Example 1, the desired product was obtained in 68% yield as an oil; NMR(CDCl₃ TMS): δ1.21 (m, 1H); 1.35 (m, 1H); 1.60 (m, 1H); 1.65 (m, 1H); 2.00 (m, 1H); 2.20 (m, 1H); 2.26 (m, 2H); 3.25 (d, 1H, J=14 Hz); 3.55 (d, 1H, J=14 Hz); 6.65 (d, 1H, J=8 Hz); 6.98 (m, 1H); 7.09 (m, 2H); 7.21 (m, 1H); 7.27 (m, 2H); 7.42 (m, 1H); 7.51 (t, 2H, J=7 Hz); 8.44 (d, 1H, J=5 Hz); 8.90 (s, 1H); IR(KBr): 1718, 1612, 1583, 1549, 1500, 1481, 1465, 1454, 1376, 1326, 1221, 758, 733, 700 cm⁻¹; mass spec m/e 383 (M+1). HRMS: m/e calcd 383.187187, m/e found 383.185396 (M+H).

EXAMPLE 22

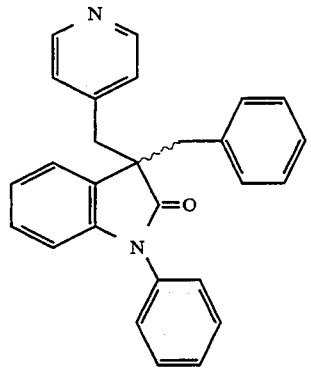

1,3-Dihydro-1-phenyl-3-(phenylmethyl)-3-(4-pyridinylmethyl)-2H-indole-2-one

By substituting benzyl bromide in Example 1, the desired product was synthesized and isolated as the free base in 89% yield; mp 127°–128° C.

EXAMPLE 23

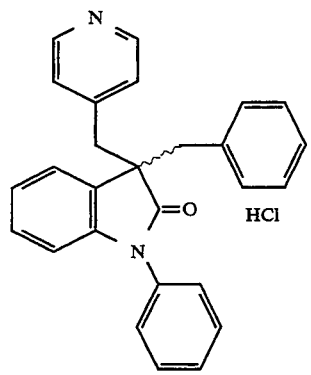

1,3-Dihydro-1-phenyl-3-(phenylmethyl)-3-(4-pyridinylmethyl)-2H-indole-2-one Hydrochloride The product in Example 22 was treated with 1N HCl/diethyl ether and the resulting hydrochloride salt was isolated in 100% yield; mp 236°–238° C.

EXAMPLE 24

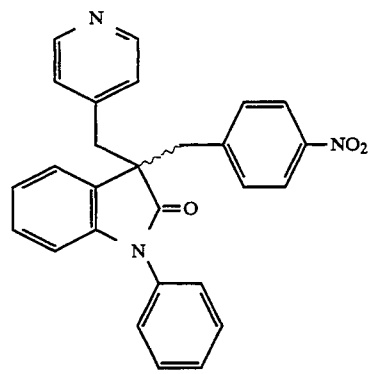

1,3-Dihydro-3-[(4-nitrophenyl)methyl]-1-phenyl-3-(4-pyridinyl-methyl)-2H-indol-2-one.

By substituting 4-nitrobenzyl bromide in Example 1, the desired product was synthesized and isolated as the free base in 76% yield; mp 168°–169° C.

EXAMPLE 25

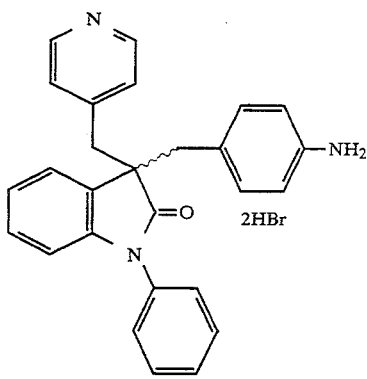

3-[(4-Aminophenyl)methyl]-1,3-dihydro-1-phenyl-3-(4-pyridinylmethyl)-2H-indol-2-one Dihydrobromide By reducing 1,3-dihydro-3-[(4-nitrophenyl)methyl]-1-phenyl-3-(4-pyridinylmethyl)-2H-indol-2-one as described in Org. Syn, Vol. 5, 346, the desired product was synthesized and isolated as the dihydrobromide salt in 70% yield; mp 200°–201° C.

EXAMPLE 26

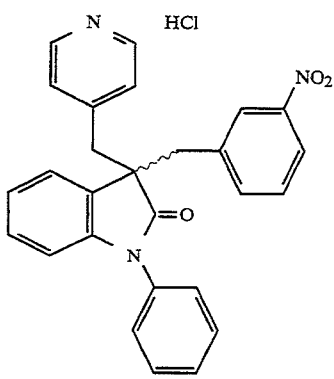

1,3-Dihydro-3-[(3-nitrophenyl)methyl]-1-phenyl-3-(4-pyridinylmethyl)-2H-indol-2-one) Hydrochloride.

By substituting 3-nitrobenzyl bromide in Example 1, the desired product was synthesized and isolated as the hydrochloride salt in 78% yield as a foam; IR(nujol): C=O @1710 cm⁻¹; NMR(DMSOd₆ TMS): δ3.5–3,9 (m, 4H, CH₂—C—CH₂), [6.25 (d, 1H), 6.71 (d, 2H), 7.1 (m, 1H), 7.19 (m, 1H), 7.44 (m, 6H), 7.60 (d, 2H), 7.90 (d, 1H), 8.0 (m, 1H), 8.72 (d, 2H), Ar]; mass spec m/e 436(M+1).

EXAMPLE 27

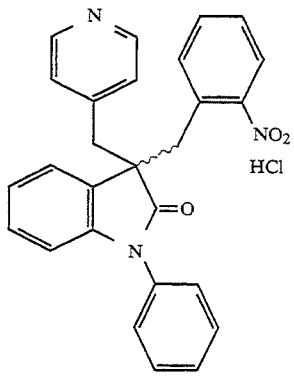

1,3-Dihydro-3-[(2-nitrophenyl)methyl]-1-phenyl-3-(4-pyridinylmethyl)-2H-indol-2-one Hydrochloride.

By substituting 2-nitrobenzyl bromide in Example 1, the desired product was synthesized and isolated in 92% yield as a foam; IR(KBr): C=O 1710 cm⁻¹; NMR(CDCl₃ TMS): δ[3.50 (d, 1), 3.73 (d, 1), 3.69 (d, 1), 4.40 (d, 1H), CH₂—C—CH₂], [6,3 (m, 6.6 (m, 2H), 7.1 (m, 2H), 7.4 (m, 9H), 7.7 (d, 1H), 8.41 (d, 2H), Ar]; mass spec m/e 436(M+1).

EXAMPLE 28

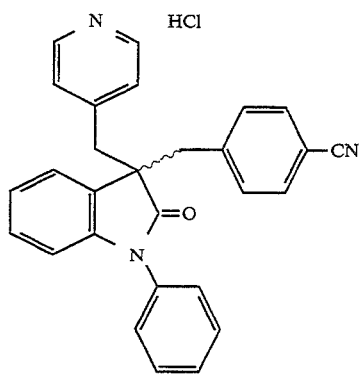

1,3-Dihydro-3-[(4-cyanophenyl)methyl]-1-phenyl-3-(4-pyridinylmethyl)-2H-indol-2-one Hydrochloride By substituting α-bromo-p-tolunitrile in Example 1, the desired product was synthesized and isolated as the hydrochloride salt in 30% yield as a foam; IR(nujol): CN @2226 and C=O @1712 cm⁻¹; NMR(DMSOd₆ TMS): δ3.4–3.8 (m, 4H, CH₂—C—CH₂), [6.25 (d, 1H), 6.72 (d, 2H), 7.07 (m, 3H), 7.47 (m, 5H), 7.58 (m, 3H), 7.86 (d, 1H), 8.66 (d, 2H), Ar], mass spec m/e 416(M+1).

EXAMPLE 29

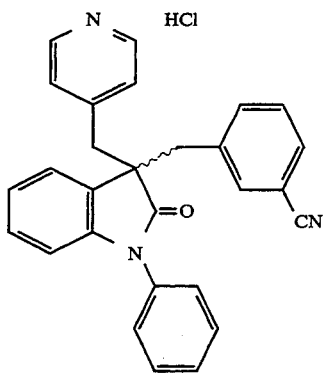

1,3-Dihydro-3-[(3-cyanophenyl)methyl]-1-phenyl-3-(4-pyridinylmethyl)-2H-indol-2-one Hydrochloride By substituting α-bromo-m-tolunitrile in Example 1, the desired product was synthesized and isolated as the hydrochloride salt in 68% yield; mp 212°–214° C.

EXAMPLE 30

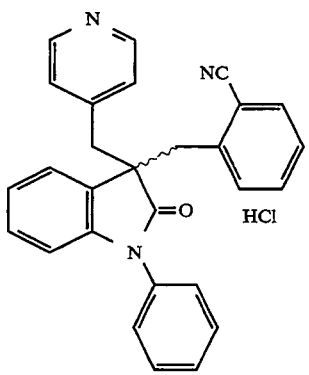

1,3-Dihydro-3-[(2-cyanophenyl)methyl]-1-phenyl-3-(4-pyridinylmethyl)-2H-indol-2-one Hydrochloride By substituting α-bromo-o-tolunitrile in Example 1, the desired product was synthesized and isolated as the hydrochloride salt in 68% yield; mp 166°–167° C. dec.

EXAMPLE 31

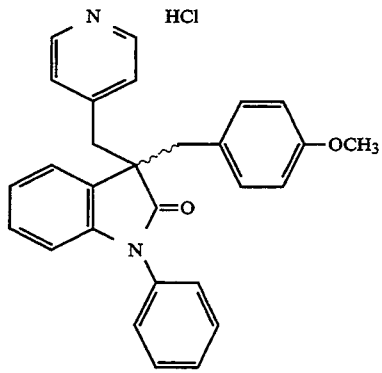

1,3-Dihydro-3-[(4-methoxyphenyl)methyl]-1-phenyl-3-(4-pyridinylmethyl)-2H-indol-2-one Hydrochloride By substituting 4-methoxybenzyl chloride in Example 1, the desired product was synthesized and isolated as the hydrochloride salt in 52% yield; mp 205°–208° C.

EXAMPLE 32

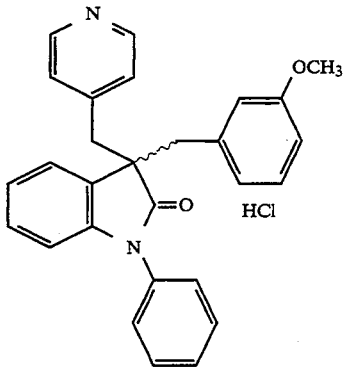

1,3-Dihydro-3-[(3-methoxyphenyl)methyl]-1-phenyl-3-(4-pyridinylmethyl)-2H-indol-2-one Hydrochloride By substituting 3-methoxybenzyl chloride in Example 1, the desired product was synthesized and isolated as the hydrochloride salt in 57% yield; mp 165°–166° C.

EXAMPLE 33

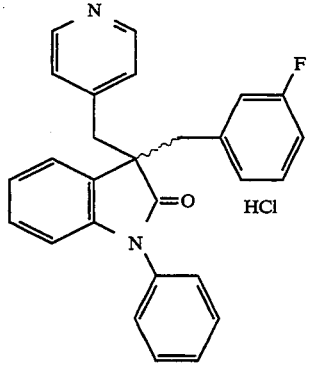

1,3-Dihydro-3-[(3-fluorophenyl)methyl]-1-phenyl-3(4-pyridinylmethyl)-2H-idol-2one Hydrochloride By substituting 3-fluorobenzyl bromide in Example 1, the desired product was synthesized and isolated as the hydrochloride salt in 78% yield; mp 210°–212° C.

EXAMPLE 34

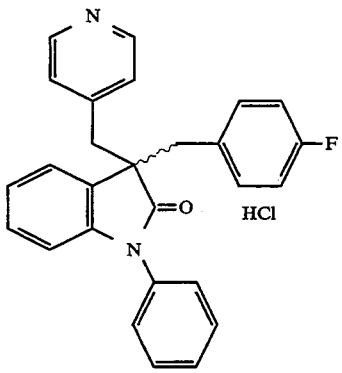

1,3-Dihydro-3-[(4-fluorophenyl)methyl]-1-phenyl-3-(4-pyridinylmethyl)-2-one Hydrochloride By substituting 4-fluorobenzyl bromide in Example 1, the desired product was synthesized and isolated as the hydrochloride salt in 76% yield; mp 225°–226° C.

EXAMPLE 35

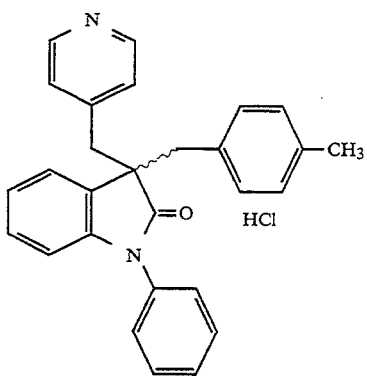

1,3-Dihydro-3-[(4-methylphenyl)methyl]-1-phenyl-3-(4-pyridinylmethyl)-2H-indol-2-one Hydrochloride By substituting α-bromo-p-xylene in Example 1, the desired product was synthesized and isolated as the hydrochloride salt in 30% yield; mp 208°–211° C.

Preparation 4

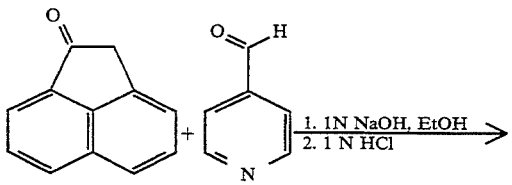

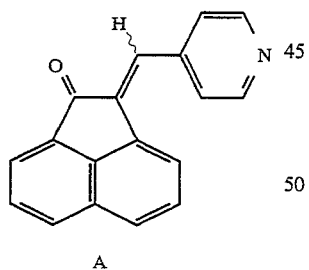

A

To a solution of acenaphthenone (33.64 g, 200 mmol) and 4-pyridine carboxaldehyde (23.56 g, 220 mmol)in 400 ml EtOH was added 50 ml 1N NaOH at room temperature, in 10 ml portions. The mixture was heated to reflux for 15 min. and allowed to cool to room temperature. The solution was cooled in an ice bath and neutralized with 1N HCl while stirring. On standing, the mixture presented orange crystals, which were collected by filtration, washed with cold 75% EtOH/H$_2$O, and dried to give the desired material in 48% (24.72 g) yield (C$_{18}$H$_{11}$ NO, MW 257.29).

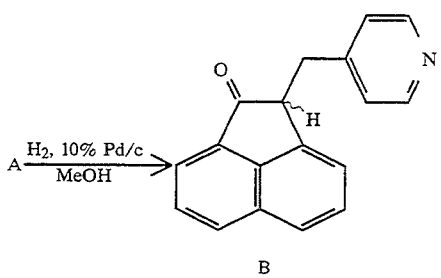

B

The olefin 4A (24.7 g) was dissolved in 250 ml MeOH and hydrogenated in a Parr Shaker over 1 g 10% Pd/c at 50 psi of hydrogen for 2 h. The catalyst was removed by filtration over Celite, and the filtrate was concentrated in vacuo to an orange oil of constant weight (26.11 g). Upon the addition of a few milliliters of EtOAc, crystals formed. The mixture was cooled, and the resulting crystals were collected by filtration, washed with cold EtOAc, and dried to give the desired starting material in 63% (15.69 g) yield as the free base yellow solid; mp 110°–112° C.; NMR(CDCl$_3$ TMS): δ3.04 (dd, 1H, J=9 Hz, 15 Hz), 3.57 (dd, 1H, J=5 Hz, 14 Hz), 4.06 (dd, 1 H, J=5 Hz, 9 Hz), 7.04 (d, 1H, J=7 Hz), 7.1 2H, J=6 Hz), 7.50 (t, 1H, J=8 Hz), 7.70 (t, 1H, J=8 Hz), 7.80 (d, 1 Hz), 7.95 (d, 1H. J=7 Hz), 8.08 (d, 1H, J=8 Hz); 8.45 (d, 2H, J=6 Hz); mass spec m/e 260(M+1); Anal calcd C$_{18}$H$_{13}$NO, MW 259.29: C, 83.38; H, 83.38; H 5.05; N, 5.40. Found: C, 82.98; H, 4.92; N, 5.18.

Preparation 5

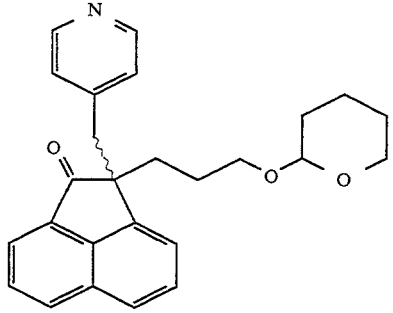

2-(4-Pyridinylmethyl)-2-[3-tetrahydro-2H-pyran-2-yloxy)propyl]-1(2H)acenaphthylenone By reacting 2-(3-bromopropyl)tetrahydro-2H-pyran with Preparation 4B as in Example 1, the desired protected alcohol was obtained in quantitative yield as an oil.

EXAMPLE 36

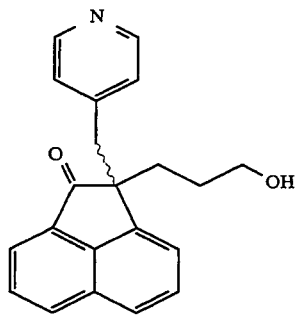

2-(3-Hydroxypropyl)-2-(4-pyridinylmethyl)-1(2H)-acenaphthylenone

By treating the "protected" alcohol, 2-(4-pyridinylmethyl)-2-[3-tetrahydro-2H-pyran-2-yloxy)propyl]-1(2H)-acenaphthylenone, with aqueous acid, the corresponding alcohol was obtained as the free base on workup in 80% yield; mp 157°–159° C.

EXAMPLE 37

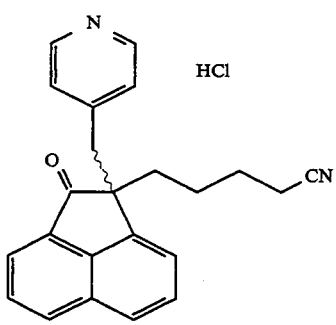

1,2-Dihydro-2-oxo-1-(4-pyridinylmethyl)-1-acenaphthylenepentanenitrile Hydrochloride By substituting 5-bromovaleronitrile and Prep 4B in Example 1, the desired product was obtained in 37% yield as the hydrochloride salt; mp 8°–221° C. The free base mp 103°–104° C.

EXAMPLE 38

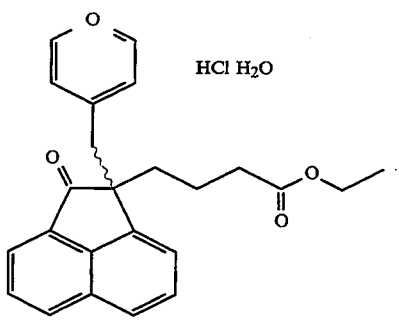

1,2-Dihydro-2-oxo-1-(4-pyridinylmethyl)-1-acenaphthylene-butanoic acid Ethyl Ester Hydrochloride Hydrate By substituting ethyl 4-bromobutyrate and Prep 4B in Example 1, the desired product was obtained in 52% yield; mp 189°–191° C.

EXAMPLE 39

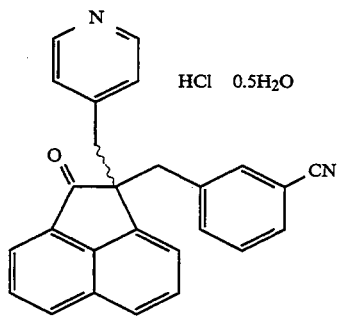

3-[(1,2-Dihydro-2-oxo-1-(4-pyridinylmethyl)-1-acenaph-ylenyl)methyl]benzonitrile Hydrochloride Hemihydrate By substituting α-bromo-m-tolunitrile and Prep 4B in Example 1, the desired product was obtained in 60% yield; mp 240°–246° C.

EXAMPLE 40

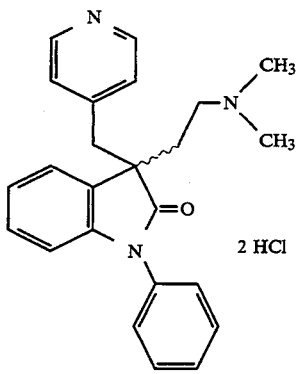

3-[2-(Dimethyl)ethyl]-1,3-dihydro-1-phenyl-3-(4-pyridinylmethyl)-2H-indol-2-one Dihydrochloride.

By substituting chloroethyl dimethylamine in Example 1, the desired product was obtained as a very hygroscopic foam in 55% yield; IR(nujol): C=O 1708 cm$^{-1}$; NMR(DMSOd$_6$ TMS): δ2.51, 2.98 (2m, 2H, N—C—CH$_2$), 2.78 (s, 6H, CH$_3$—N—CH$_3$), [3.46 (m, 2H), 3.67 (d, 1H), 4.03 (t, 1H) CH$_2$—C—CH$_2$], [6.54 (m, 1H), 7.23 (m, 2H), 7.75 (m, 1H), 1,2-Phe], [7.12 (d, 2H), 7.48 (m, 1H), 7.54 (m, 2H), Phe], [7.37, 8.63 (2d, 4H, 4-Pyr)]; mass spec m/e 372(M+1)-2HCl.

EXAMPLE 41

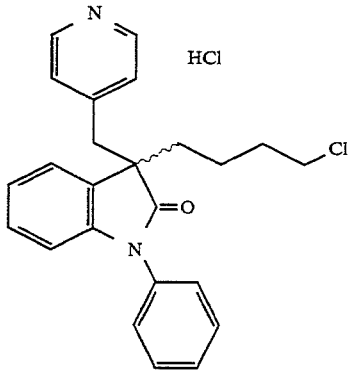

3-(4-Chlorobutyl)-1,3-dihydro-1-phenyl-(4-pyridinylmethyl)-2H-indol-2-one Hydrochloride By substituting 1-bromo-4-chlorobutane in Example 1, the desired product was obtained in 82% yield; mp 149°–151° C.

EXAMPLE 42

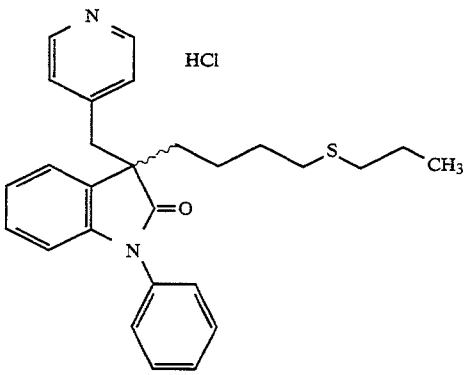

1,3-Dihydro-1-phenyl-3[4-(propylthio)butyl]-3-(4-pyridinylmethyl)-2H-indol-2-one Hydrochloride 3-(4-Chlorobutyl)-1,3-dihydro-1-phenyl-(4-pyridinylmethyl)-2H-indol-2-one hydrochloride (6.0 g, 14.04 mmol) in 75 ml dry THF was treated with NaH (0.75 g, 31.25 mmol) and stirred for 10 min. under dry nitrogen. The mixture was then treated with propanethiol (1.2 g, 15.4 mmol) and stirred at room temperature for 16 h. The mixture was concentrated in vacuo, and the residue was partitioned between 150 ml $CH_2Cl_2$ and 100 ml water. The organic layer was washed with water and brine, dried over $MgSO_4$, filtered, treated with 20 ml 1N HCl/ether, and evaporated to dryness. The residue was triturated with 100 ml hot EtOAc, cooled to room temperature, and filtered to collect the solid. The solid was dried in vacuo to give the product in 81% (5.3 g) yield; mp 149°–150° C.; IR(KBr): C=O 1717 cm$^{-1}$; NMR(DMSOd$_6$ TMS): δ0.90 (t, 3H, CH$_3$), 1.02, 1.18 (2m, 2H, SCCCH$_2$), 1.45 (m, 4H, CH$_2$CSCCH$_2$), 2.1 (SCCCCH$_2$), 2.37 (2t, 4H, CH$_2$SCH$_2$), [3.42 (d, 1H), 3.59 (d, 1H), CH$_2$-Pyr], [6.53 (m, 1H), 7.19 (m, 2H), 7.44 (d, 3H), 7.53 (m, 2H), 7.65 (m, 1H) Ar], 7.10, 8.66 (2d, 4H, 4-Pyr]; mass spec m/e 431 (M+1)-HCl.

EXAMPLE 43

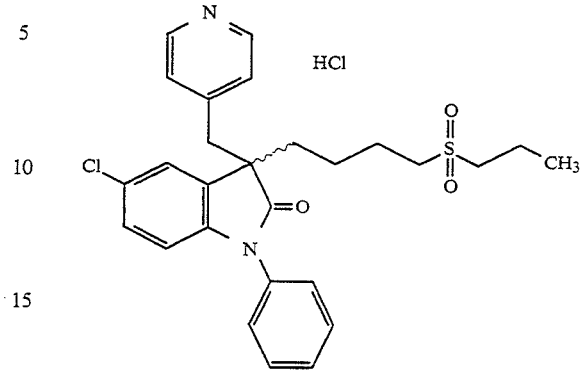

5-Chloro-1,3-dihydro-1-phenyl-3-[4-propylsulfonyl)-butyl]-3(3-(4-pyridinylmethyl)-2H-indol-2-one Hydrochloride.

1,3-Dihydro-1-phenyl-3-[4-(propylthio)butyl]-3-(4-pyridinylmethyl)2N-indol-2-one hydrochloride (2.0 g, 4.28 mmol) in 50 ml MeOH and 11 ml water was treated with OXONE (monopersulfate compound, 2KHSO$_5$/KHSO$_4$/K$_2$SO$_4$) (7.9 g, 12.85 mmol) and stirred for 16 h. The reaction mixture was concentrated in vacuo, and the residue was partitioned between 100 ml 1N NaOH and 100 ml CH$_2$Cl$_2$. The organic phase was washed with water and brine, dried over MgSO$_4$, filtered, and concentrated to an oil. The oil was column chromatographed on silica gel using CHCl$_3$-MeOH (10:1) as the mobile phase, and appropriate fractions were combined and concentrated to an oil. The oil was triturated with 1N HCl/ether to give a solid which was collected by filtration, washed with ether, and dried in vacuo to give the product in 70% (1.6 g) yield; mp 197°–199° C. dec.; IR(nujol): C=O 1711, SO2 1141 cm$^{-1}$; NMR(CDCl$_3$ TMS): δ1.07 (t, 3H, CH$_3$), 1.3 (m, 2H, SCCCH$_2$), 1.8 (m, 4H, CH$_2$CSCCH$_2$), 2.1, 2.3 (2m, 2H, SCCCCH$_2$), 2.9 (m, 4H, CH$_2$SCH$_2$), 3.3–3.6 (m, 2H, CH$_2$-Pyr), [6.57 (d, 1H), 7.2 (d, 1H), 7.4 (m 6H) Ar], 6.92, 8.48 (2d, 4H, 4-Pyr]; mass spec m/e 497(M+1).

EXAMPLE 44

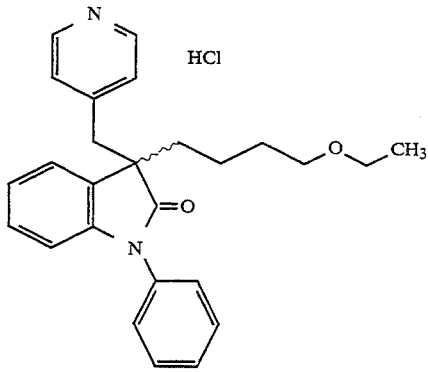

1,3-Dihydro-1-phenyl-3-[4-(ethyloxy)butyl]-3-(4-pyridinylmethyl)-2H-indol-2-one Hydrochloride By substituting potassium ethoxide for sodium hydride+propanethiol in Example 42, the desired product was obtained in 73% yield; mp 95°–98° C.

EXAMPLE 45

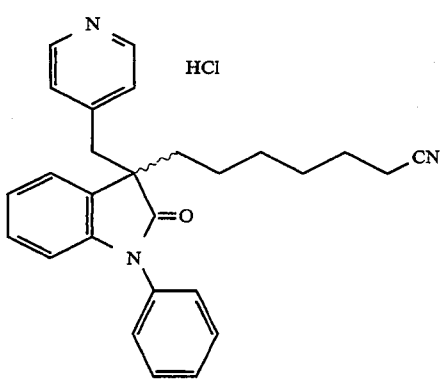

2,3-Dihydro-2-oxo-1-phenyl-3-(4-pyridinylmethyl)-1H-indole-3-heptanenitrile Hydrochloride By substituting 7-bromoheptanenitrile in Example 1, the desired product was obtained in 11% yield; mp 190°–192° C.

EXAMPLE 46

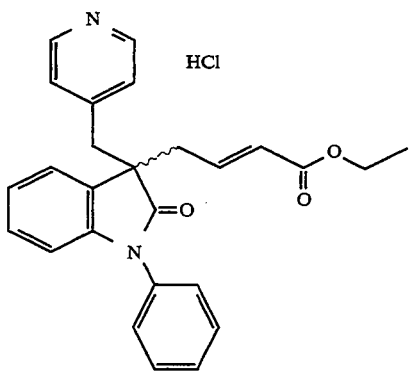

4-[2,3-Dihydro-2-oxo-1-phenyl-3-(4-pyridinylmethyl)-1H-indol-3-yl]-2-butenoic Acid Ethyl Ester Hydrochloride.

By substituting ethyl 4-bromocrotonate in Example 1, the desired product was obtained as an oil in 56% yield; IR(neat): C=O 1718 cm$^{-1}$; NMR(CDCl$_3$ TMS): δ1.24 (t, 3H, CH$_3$), 2.94 (m, 2H, CH$_2$—C=C), [3.11 (d, 1H, J12), 3.32 (d, 1H, J12), CH$_2$-Pyr], 4.14 (q, 2H, OCH$_2$), 5.90 (d, 1H, J16, C=CH—CO), 6.7 (m, 1H, CH=C—CO), [6.5 (m, 1H), 6.79 (d, 2H), 6.9 (d, 2H), 7.15 (m, 2H), 7.4 (m, 4H), 8.29 (d, 2H), Ar]; mass spec m/e 413(M+1).

EXAMPLE 47

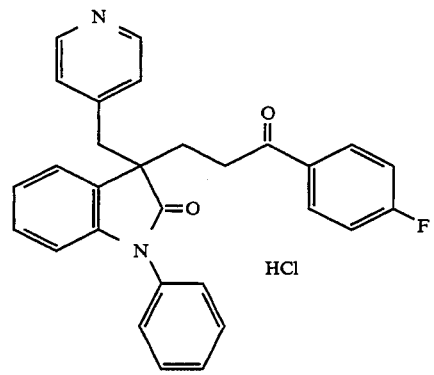

3-[3,4-(4-Fluorophenyl)-3-oxopropyl]-1,3-dihydro-1-phenyl-3-(4-pyridinylmethyl)-2H-indol-2-one Hydrochloride.

By substituting 3-chloro-4-fluoropropiophenone in Example 1, the desired product was obtained in 65% yield; mp 183°–185° C. dec.

EXAMPLE 46

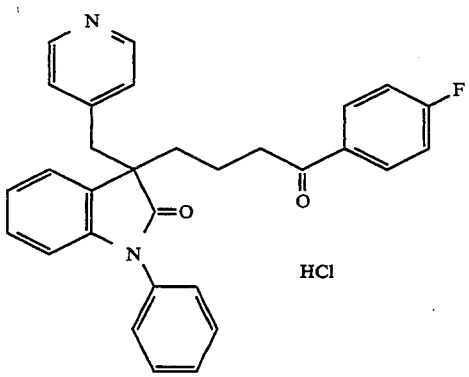

3-[4-(4-Fluorophenyl)-4-oxobutyl]-1,3-dihydro-1-phenyl-3-(4-pyridinylmethyl)-2H-indol-2-one Hydrochloride.

By substituting 4-chloro-4-fluorobutyrophenone propylene ketal in Example 1, the corresponding ketal was obtained, which was converted by standard methods to the ketone in 46% yield; mp 205° C. dec.

EXAMPLE 49

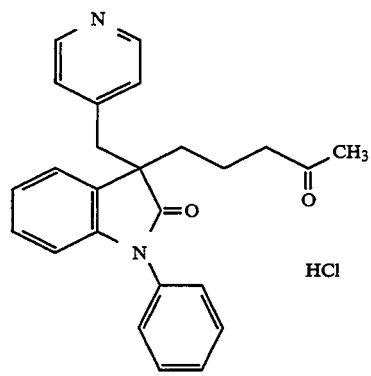

5-[2,3-Dihycro-2-oxo-1-phenyl-3-(4-pyridinylmethyl)-1H-indol-3-yl]-2-pentanone Hydrochloride.

By substituting 5-chloro-2-pentanone ethylene ketal in Example 1, the corresponding ketal was obtained, which was converted to the ketone in 44% yield; mp 192°–194° C.

EXAMPLE 50

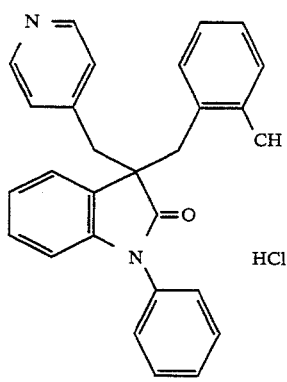

1,3-Dihydro-3-[(2-methylphenyl)methyl]-1-phenyl-3-(4-pyridinylmethyl)-2H-indol-2-one Hydrochloride By substituting α-bromo-o-xylene in Example 1, the desired product was obtained in 80% yield; mp 150°–153° C.

EXAMPLE 51

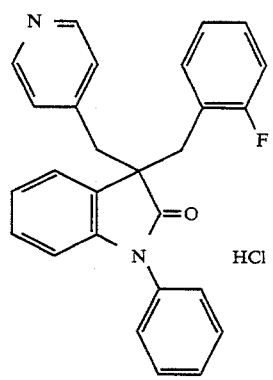

1,3-Dihydro-3-[(2-fluorophenyl)methyl]-1-phenyl-3-(4-pyridinylmethyl)-2H-indol-2-one Hydrochloride By substituting 2-fluorobenzyl bromide in Example 1; the desired product was obtained in 79% yield; mp 195°–198° C.

EXAMPLE 52

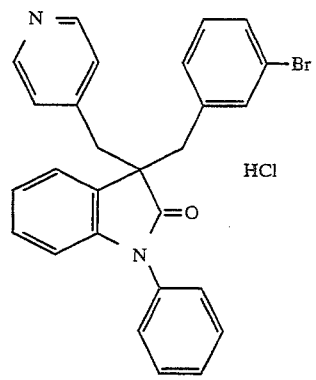

1,3-Dihydro-3-[(3-bromophenyl)methyl]-1-phenyl-3-(4-pyridinylmethyl)-2H-indol-2-one Hydrochloride By substituting 3-bromobenzyl bromide in Example 1;the desired product was obtained in 98% yield as a foam; IR(KBr): C=O @1711 cm$^{-1}$; NMR(CDCl$_3$ TMS): δ[3.30, 3.43 (2d, 2H), 3.58, 3.72 (2d, 2H), CH$_2$—C—CH$_2$)], [6.29(d, 1H), 6.67 (d, 2H), 6.81 (d, 1H), 6.92 (dd, 1H), 7.07 (d, 2H), 7.12 (d, 1H), 7.24 (d, 1H), 7.33 (m, 3H), 7.57 (d, 2H), 8.52 (d, 2H) Ar]; mass spec m/e 469(M+1).

EXAMPLE 53

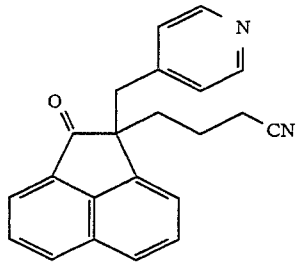

1,2-Dihydro-2-oxo-1-(4-pyridinylmethyl)-1-acenaphthylenebutanenitile.

By substituting 4-bromobutyronitrile and Preparation 4 in Example 1, the desired product was obtained in 81% yield; mp 93°–95° C.

EXAMPLE 54

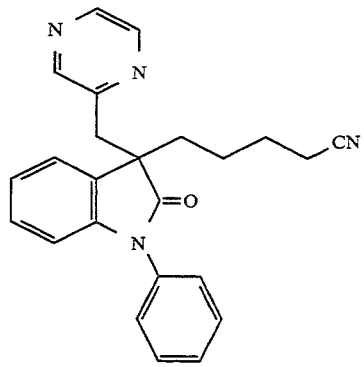

2,3-Dihydro-2-oxo-1-phenyl-3-(2-pyrazinylmethyl)-1H-indole-3-pentanenitrile.

By substituting 2,3-dihydro-2-oxo-1-phenyl-3-(2-pyrazinylmethyl)1H-indole and 5-bromovaleronitrile in Example 1, the desired product was obtained in 76% yield as an oil.

EXAMPLE 55

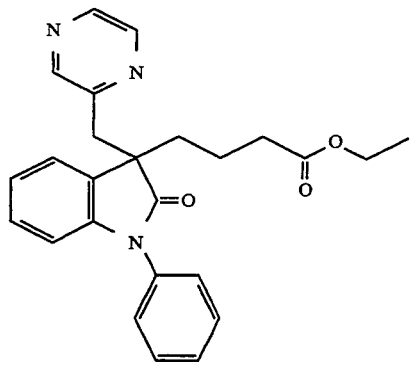

2,3-Dihydro-2-oxo-1-phenyl-3-(2-pyrazinylmethyl)-1H-indole-3-butanoic Acid Ethyl Ester.

By substituting 2,3-dihydro-2-oxo-1-phenyl-3-(2-pyrazinylmethyl)-1H-indol and ethyl 4-bromobutyrate in Example 1, the desired product was obtained in 80% yield as an oil.

By using the methods in the examples above, the following compounds of this invention can be synthesized:

TABLE I (Structures)

| Ex. | Q | $R^1$ | $R^2$ | $R^3$ | $R^4$ | $R^5$ |
|---|---|---|---|---|---|---|
| 56 | Oxindole | 2-F,4-Pyr | Phe | H | H | $(CH_2)_3CO_2Et$ |
| 57 | Oxindole | 2-F,4-Pyr | Phe | H | H | $(CH_2)_4CN$ |
| 58 | Acenaphthenone | 2-F,4-Pyr | | H | H | $(CH_2)_3CO_2Et$ |
| 59 | Acenaphthenone | 2-F,4-Pyr | | H | H | $(CH_2)_4CN$ |
| 60 | Oxindole | 3-Pyr | Phe | H | H | $(CH_2)_3CO_2Et$ |
| 61 | Oxindole | 3-Pyr | Phe | H | H | $(CH_2)_4CN$ |
| 62 | Oxindole | 3-Pyr | Phe | H | H | $CH_2$—(3-CN—Phe) |
| 63 | Oxindole | 2-Pyr | Phe | H | H | $(CH_2)_3CO_2Et$ |
| 64 | Acenaphthenone | 4-Pyr | | 4-Cl | 6-$CH_3O$ | $CH_2$—(3-CN—Phe) |
| 65 | Acenaphthenone | 4-Pyr | | 5-$CH_3$ | H | $CH_2$—(3-CN—Phe) |
| 66 | Acenaphthenone | 4-Pyr | | 3-CN | H | $(CH_2)_4CN$ |
| 67 | Acenaphthenone | 4-Pyr | | 3-CN | H | $CH_2$—(3-CN—Phe) |
| 68 | Oxindole | 2-Pyr | Phe | H | H | $(CH_2)_4CN$ |
| 69 | Oxindole | 2-Pyr | Phe | H | H | $CH_2$—(3-CN—Phe) |
| 70 | Oxindole | 4-Pyr | 4-$NH_2$—Phe | H | H | $(CH_2)_3CO_2Et$ |
| 71 | Oxindole | 4-Pyr | 4-$NO_2$—Phe | H | H | $(CH_2)_3CO_2Et$ |
| 72 | Oxindole | 4-Pyr | 4-Cl—Phe | H | H | $(CH_2)_3CO_2Et$ |
| 73 | Oxindole | 4-Pyr | 4-Me—Phe | H | H | $(CH_2)_3CO_2Et$ |
| 74 | Oxindole | 4-Pyr | 4-$CF_3$—Phe | H | H | $(CH_2)_3CO_2Et$ |
| 75 | Oxindole | 4-Pyr | 4-Br—Phe | H | H | $(CH_2)_3CO_2Et$ |
| 76 | Oxindole | 4-Pyr | 4-F—Phe | H | H | $(CH_2)_3CO_2Et$ |
| 77 | Oxindole | 4-Pyr | 4-$MeSO_2$—Phe | H | H | $(CH_2)_3CO_2Et$ |
| 78 | Oxindole | 4-Pyr | 4-$NH_2$—Phe | H | H | $(CH_2)_4CN$ |
| 79 | Oxindole | 4-Pyr | 4-$NO_2$—Phe | H | H | $(CH_2)_4CN$ |
| 80 | Oxindole | 4-Pyr | 4-Cl—Phe | H | H | $(CH_2)_4CN$ |
| 81 | Oxindole | 4-Pyr | 4-Me—Phe | H | H | $(CH_2)_4CN$ |
| 82 | Oxindole | 4-Pyr | 4-$CF_3$—Phe | H | H | $(CH_2)_4CN$ |
| 83 | Oxindole | 4-Pyr | 4-Br—Phe | H | H | $(CH_2)_4CN$ |
| 84 | Oxindole | 4-Pyr | 4-F—Phe | H | H | $(CH_2)_4CN$ |
| 85 | Oxindole | 4-Pyr | 4-$CH_3SO_2$—Phe | H | H | $(CH_2)_4CN$ |
| 86 | Oxindole | 4-Pyr | 4-$NH_2$—Phe | H | H | $CH_2$—(3-CN-Phe) |
| 87 | Oxindole | 4-Pyr | 4-$NO_2$—Phe | H | H | $CH_2$—(3-CN-Phe) |
| 88 | Oxindole | 4-Pyr | 4-Cl—Phe | H | H | $CH_2$—(3-CN-Phe) |
| 89 | Oxindole | 4-Pyr | 4-$CH_3$—Phe | H | H | $CH_2$—(3-CN-Phe) |
| 90 | Oxindole | 4-Pyr | 4-$CF_3$—Phe | H | H | $CH_2$—(3-CN-Phe) |
| 91 | Oxindole | 4-Pyr | 4-Br—Phe | H | H | $CH_2$—(3-CN-Phe) |
| 92 | Oxindole | 4-Pyr | 4-F—Phe | H | H | $CH_2$—(3-CN-Phe) |
| 93 | Oxindole | 4-Pyr | 4-$CH_3SO_2$—Phe | H | H | $CH_2$—(3-CN-Phe) |
| 94 | Oxindole | 4-Pyr | Phe | 5-$NO_2$— | H | $(CH_2)_3CO_2Et$ |
| 95 | Oxindole | 4-Pyr | Phe | 5-Cl— | H | $(CH_2)_3CO_2Et$ |
| 96 | Oxindole | 4-Pyr | Phe | 5-$NH_2$— | H | $(CH_2)_3CO_2Et$ |
| 97 | Oxindole | 4-Pyr | Phe | 5-$CH_3$ | H | $(CH_2)_3CO_2Et$ |
| 98 | Oxindole | 4-Pyr | Phe | 5-$CF_3$— | H | $(CH_2)_3CO_2Et$ |

TABLE I-continued

| | | | (Structures) | | |
|---|---|---|---|---|---|
| Ex. | Q | R¹ | R² | R³ | R⁴ | R⁵ |

| Ex. | Q | R¹ | R² | R³ | R⁴ | R⁵ |
|---|---|---|---|---|---|---|
| 99 | Oxindole | 4-Pyr | Phe | 5-MeSO₂— | H | (CH₂)₃CO₂Et |
| 100 | Oxindole | 4-Pyr | Phe | 5-F— | H | (CH₂)₃CO₂Et |
| 101 | Oxindole | 4-Pyr | Phe | 5-Br— | H | (CH₂)₃CO₂Et |
| 102 | Oxindole | 4-Pyr | Phe | 5-CH₃O | H | (CH₂)₃CO₂Et |
| 103 | Oxindole | 4-Pyr | Phe | 5-N(CH₃)₂ | H | (CH₂)₃CO₂Et |
| 104 | Oxindole | 4-Pyr | Phe | 5-NHCH₃ | H | (CH₂)₃CO₂Et |
| 105 | Oxindole | 4-Pyr | Phe | 5-CH₃S— | H | (CH₂)₃CO₂Et |
| 106 | Oxindole | 4-Pyr | Phe | 5-CH₃SO | H | (CH₂)₃CO₂Et |
| 107 | Oxindole | 4-Pyr | 4-CH₃O—Phe | 5-CH₃O— | 6-NO₂ | (CH₂)₃CO₂Et |
| 108 | Oxindole | 4-Pyr | Phe | 5-F | 6-F | (CH₂)₃CO₂Et |
| 109 | Oxindole | 4-Pyr | 4-CN—Phe | 5-CN | 6-CN | (CH₂)₃CO₂Et |
| 110 | Acenaphthenone | 4-Pyr | | 5-NO2 | H | (CH₂)₃CO₂Et |
| 111 | Acenaphthenone | 4-Pyr | | 5-F | H | (CH₂)₃CO₂Et |
| 112 | Acenaphthenone | 4-Pyr | | 5-CH₃ | H | (CH₂)₃CO₂Et |
| 113 | Acenaphthenone | 4-Pyr | | 4-Cl | 6-CH₃O | (CH₂)₃CO₂Et |
| 114 | Acenaphthenone | 4-Pyr | | 3-Br | H | (CH₂)₃CO₂Et |
| 115 | Acenaphthenone | 4-Pyr | | H | 6-NO₂ | (CH₂)₃CO₂Et |
| 116 | Acenaphthenone | 4-Pyr | | 3-CN | H | (CH₂)₃CO₂Et |
| 117 | Acenaphthenone | 4-Pyr | | 5-NO₂ | H | (CH₂)₄CN |
| 118 | Acenaphthenone | 4-Pyr | | 5-F | H | (CH₂)₄CN |
| 119 | Acenaphthenone | 4-Pyr | | 5-CH₃ | H | (CH₂)₄CN |
| 120 | Acenaphthenone | 4-Pyr | | 4-Cl | 6-CH₃O | (CH₂)₄CN |
| 121 | Acenaphthenone | 4-Pyr | | 3-Br | H | (CH₂)₄CN |
| 122 | Acenaphthenone | 4-Pyr | | H | 6-NO₂ | (CH₂)₄CN |

(Pyr = Pyridyl)

Biochemical Test Procedure

Neurotransmitter release assay. The neurotransmitter release activities of the compounds of this invention were determined as reported by Nickolson, et al., (1990) Drug Development Research, 19, 285-300 of a modification of the procedure described by Mulder, et al., Brain Res., 1974, 70, 372.

Male Wistar rats (Charles River) weighing 175-200 grams were used. The rats were housed for at least seven days before the experiment in animal facility under 12/12 hour light/dark cycle. Deionized water and standard rat chow (Purina) were available ad libitum.

Rats were decapitated and brains were dissected immediately. Slices (0.3 mm thick) from the parietal cortex were prepared manually using a recessed Lucite guide and subsequently cut into 0.25×0.25 mm squares.

Slices (approximately 100 mg wet weight) were incubated in 10 ml KrebsRinger medium (KR) containing NaCl (116 mM), KCl (3 mM), CaCl₂ (1.3 mM), MgCl₂(1.2 mM), KH₂PO₄(1.2 mM), Na₂SO₄ (1.2 mM), NaHCO₃(25.0 mM), and glucose (11.0 mM), to which was added 10 uCi ³H-choline (specific activity approximately 35 Ci/mM; NEN) and 10 mM unlabeled choline to give a final concentration of one micromole. The brain preparations were incubated for 30 min. at 37° C. under a steady flow of 95% O₂/5% CO₂. Under these conditions, part of the radioactive choline taken up by the preparation was converted into radioactive acetylcholine (ACh) by the cholinergic nerve endings stored in synaptic vesicles, and released upon depolarization by high potassium ion (K+) containing media.

After labelling of the ACh stores, the slices were washed three times with non-radioactive KR medium and transferred to a superfusion apparatus to measure the drug effects on ACh release. The superfusion apparatus consisted of 10 thermostated glass columns of 5 mm diameter that were provided with GF/F glass fiber filters to support the slices (approximately 10 mg tissue/column). Superfusion was carried out in KR-medium (0.3 ml/min.) containing 10 mM hemicholine-3 (HC-3). The HC-3 prevents the reuptake of choline formed during the superfusion from phospholipids and released ACh, which would be converted into unlabeled ACh and released in preference to the pre-formed labeled ACh. The medium was delivered by a 25-channel peristaltic pump (Ismatec by Brinkman) and warmed to 37° C. in a thermostated stainless steel coil before entering the superfusion column. Each column was provided with a 4-way slider valve (Beckmann instruments) which allowed rapid change of low to high K+/KR-medium, and with two 10-channel 3-way valves that were used to change from drug-free to drug-containing low and high K+/KR-medium. After 15 min. of washout of non-specifically bound radioactivity, collection of 4 min. fractions was initiated. After three 4 min. collections, the original medium was changed to a KR-medium in which the KCl concentration had been increased to 25 mM (high K+medium) (S1). Depolarization-induced stimulation of release by high K+/KR-medium lasted for 4 min. Drug free low and high K+/KR-media were then substituted by drug- and vehicle-containing low- and high- K+/KR-medium, and superfusion was continued for three 4 min. collections with low K+/KR-medium, one 4 min. collection with high K+/KR-medium (S2), and two 4 min. collections with low K+/KR-medium.

Drug was added to the media by 100-fold dilutions of appropriate concentrations of the drug (in 0.9% saline) with either low- or high- K+/KR-medium.

All superfusion fractions were collected in liquid scintillation counting vials. After superfusion, the slices were removed from the superfusion columns and extracted with 1.0 ml of 0.1N HCl. Liquiscint (NEN) counting fluid (12 ml) was added to superfusion fractions and extracts, and the samples were counted in a Packard Tricarb Liquid Scintillation Counter. No corrections were made for quenching.

The ratio of S2/S1 (as compared to controls where no drug was present during S2) was a measure of the ability of the drug to enhance or depress stimulus-induced acetylcholine release.

TABLE II

% Increase of Stimulus-induced ACh Release In Rat Cerebral Cortex In vitro at 10 uM

| Ex. | Q | $R^1$ | $R^5$ | % Yield | mp. °C. | % ACh Rel |
|---|---|---|---|---|---|---|
| 1 | Oxindole | 4-Pyr HCl | $(CH_2)_3CO_2Et$ | 86 | 182–183 | 392 |
| 2 | Oxindole | 4-Pyr HA | $(CH_2)_3CO_2Et$ | 25 | 135–136 | 294 |
| 3 | Oxindole | 4-Pyr HCl | $(CH_2)_3CO_2Et$ | 100 | foam | 587 |
| 4 | Oxindole | 4-Pyr HA | $(CH_2)_3CO_2Et$ | 56 | 132–133 | 100 |
| 5 | Oxindole | 4-Pyr HCl | $(CH_2)_3CO_2Et$ | 94 | foam | 101 |
| 6 | Oxindole | 4-Pyr HCl | $(CH_2)_1CO_2Et$ | 66 | 170–173 | 257 |
| 7 | Oxindole | 4-Pyr HCl | $(CH_2)_2CO_2Et$ | 94 | 181–182 | 112 |
| 8 | Oxindole | 4-Pyr HCl | $(CH_2)_2CO_2Me$ | 76 | 197–198 | 200 |
| 9 | Oxindole | 4-Pyr HCl | $(CH_2)_4CO_2Et$ | 83 | 172–174 | 106 |
| 10 | Oxindole | 4-Pyr HCl | $(CH_2)_1CN$ | 82 | 221 dec | 121 |
| 11 | Oxindole | 4-Pyr HCl | $(CH_2)_3CN$ | 41 | 185–187 | 236 |
| 12 | Oxindole | 4-Pyr HCl | $(CH_2)_4CN$ | 93 | 164–165 | 362 |
| 13 | Oxindole | 4-Pyr HCl | $(CH_2)_5CN$ | 42 | 191–192 | 237 |
| 14 | Oxindole | 4-Pyr HCl | $(CH_2)_4OAc$ | 87 | 170–172 | 152 |
| 15 | Oxindole | 4-Pyr | $(CH_2)_0OAc$ | 88 | 193–195 | 119 |
| 16 | Oxindole | 4-Pyr HCl | $(CH_2)_4OH$ | 30 | 196–197 | 190 |
| 17 | Oxindole | 4-Pyr | $(CH_2)_3OH$ | 50 | 146–147 | 123 |
| 18 | Oxindole | 4-Pyr HCl | $(CH_2)_2OH$ | 55 | 193, dec | 122 |
| 19 | Oxindole | 4-Pyr HCl | $(CH_2)_3CONH_2$ | 72 | 232, dec | 122 |
| 20 | Oxindole | 4-Pym | $(CH_2)_3CO_2Et$ | 55 | oil | 124 |
| 21 | Oxindole | 4-Pym | $(CH_2)_4CN$ | 68 | oil | 114 |
| 22 | Oxindole | 4-Pyr | $CH_2$—Phe | 89 | 127–128 | 210 |
| 23 | Oxindole | 4-Pyr HCl | $CH_2$—Phe | 100 | 236–238 | 219 |
| 24 | Oxindole | 4-Pyr | $CH_2$—(4-$NO_2$—Phe) | 76 | 168–169 | 125 |
| 25 | Oxindole | 4-Pyr HBr | $CH_2$—(4-$NH_2$—Phe) | 70 | 200–201 | 175 |
| 26 | Oxindole | 4-Pyr HCl | $CH_2$—(3-$NO_2$—Phe) | 78 | foam | 140 |
| 27 | Oxindole | 4-Pyr HCl | $CH_2$—(2-$NO_2$—Phe) | 92 | foam | 101 |
| 28 | Oxindole | 4-Pyr HCl | $CH_2$—(4-CN—Phe) | 30 | foam | 153 |
| 29 | Oxindole | 4-Pyr HCl | $CH_2$—(3-CN—Phe) | 68 | 212–214 | 180 |
| 30 | Oxindole | 4-Pyr HCl | $CH_2$—(2-CN—Phe) | 68 | 166–167 | 118 |
| 31 | Oxindole | 4-Pyr HCl | $CH_2$—(4-MeO—Phe) | 52 | 205–208 | 106 |
| 32 | Oxindole | 4-Pyr HCl | $CH_2$—(3-MeO—Phe) | 57 | 165–166 | 138 |
| 33 | Oxindole | 4-Pyr HCl | $CH_2$—(3-F—Phe) | 78 | 210–212 | 141 |
| 34 | Oxindole | 4-Pyr HCl | $CH_2$—(4-F—Phe) | 76 | 225–226 | 109 |
| 35 | Oxindole | 4-Pyr HCl | $CH_2$—(4-Me—Phe) | 30 | 208–211 | 118 |
| 36 | Acenaphthenone | 4-Pyr HCl | —$(CH_2)_3$—OH | 55 | 157–159 | 101 |
| 37 | Acenaphthenone | 4-Pyr HCl | $(CH_2)_4CN$ | 37 | 218–221 | 181 |
| 38 | Acenaphthenone | 4-Pyr HCl | $(CH_2)_3CO_2Et$ | 52 | 189–191 | 139 |
| 39 | Acenaphthenone | 4-Pyr HCl 0.5 $H_2O$ | $CH_2$—Phe(3-CN) | 82 | 240–246 | 218 |
| 40 | Oxindole | 4-Pyr HCl | $(CH_2)_2$—$NMe_2$HCl | 55 | foam | 105 |
| 41 | Oxindole | 4-Pyr HCl | $(CH_2)_4$—Cl | 84 | 149–151 | 111 |
| 42 | Oxindole | 4-Pyr HCl | $(CH_2)_4$—S—$C_3H_7$ | 81 | 149–150 | 100 |
| 43 | 5-Cl—Oxindole | 4-Pyr HCl | $(CH_2)_4$—$SO_2$—$C_3H_7$ | 70 | 197–199 | 119 |
| 44 | Oxindole | 4-Pyr HCl | $(CH_2)_6$—CN | 11 | 190–192 | 110 |
| 45 | Oxindole | 4-Pyr HCl | $(CH_2)_4$—O—$C_2H_5$ | 73 | 95–97 | |
| 46 | Oxindole | 4-Pyr HCl | $CH_2$—CH—CH— | 56 | oil | 121 |

TABLE II-continued

| | | | % Increase of Stimulus-induced ACh Release In Rat Cerebral Cortex In vitro at 10 uM | | | |
|---|---|---|---|---|---|---|
| Ex. | Q | $R^1$ | $R^5$ | % Yield | mp. °C. | % ACh Rel |
| 47 | Oxindole | 4-Pyr HCl | $CH_2CH_2$—CO(4-F—Phe) | 65 | 183–185, dec | 101 |
| 48 | Oxindole | 4-Pyr HCl | $CH_2CH_2CH_2$—CO—(F—Phe) | 46 | 205, dec. | 104 |
| 49 | Oxindole | 4-Pyr HCl | $CH_2CH_2CH_2$—CO—$CH_3$ | 44 | 192–194, dec. | 150 |
| 50 | Oxindole | 4-Pyr HCl | $CH_2$—(2-Me—Phe) | 80 | 150–153 | 165 |
| 51 | Oxindole | 4-Pyr HCl | $CH_2$—(2-F—Phe) | 79 | 195–198 | 127 |
| 52 | Oxindole | 4-Pyr HCl | $CH_2$—(3-Br—Phe) | 98 | foam | 128 |
| 53 | Acenaphthenone | 4-Pyr | $(CH_2)_3$—CN | 81 | 93–95 | 150 |
| 54 | Oxindole | 2-Pyrazine | $(CH_2)_4$—CN | 76 | oil | 150 |
| 55 | Oxindole | 2-Pyrazine | $(CH_2)_3$—$CO_2Et$ | 80 | oil | 150 |

Using a similar procedure, the compounds of this invention have been shown to enhance the release of dopamine (DA) as shown in Table III.

TABLE III

| Acetylcholine and Dopamine (DA) Release at Dosing of 10 uM. | | |
|---|---|---|
| Example | % DA Rel | % ACh Rel |
| 1 | 347 | 392 |
| 5 | 232 | 257 |

Behavioral Test Procedure.

Rat Passive Avoidance (PA) Hypoxia Induced Amnesia: Unfasted male CD rats, weighing between 165–210 g were trained in a PA apparatus using the following procedure: rats were placed in the clear side of the two compartment chamber and allowed 90 seconds to enter the dark compartment. Ten seconds after entering the dark chamber, a 3 second footshock (1.0 mA) was applied to the grid floor followed by an additional 10 second delay, and another 3 second footshock was applied. Retentions were tested 4 hours later. The rats were allowed 300 seconds to enter the dark compartment; time was taken. Memory disruption was induced by exposing the rats to a gas mixture containing 6.5% oxygen supplemented with nitrogen for 30 minutes before passive avoidance training. Doses of the test compound were administered (0.1 ml/100 g s.c.) relative to time of PA training. Typical results are shown in Table IV for Ex 1.

TABLE IV

| Rat Passive Avoidance-Hypoxia Induce Amnesia for Example 1. Median Retention Latencies | | |
|---|---|---|
| Dose, mg/kg | n (# animals tested) | Median Latencies, sec |
| No Hypoxia | 60 | 300.0 |
| Vehicle | 59 | 15.0 |
| 0.1 | 12 | 79.5 |
| 0.3 | 12 | 37.5 |
| 1.0 | 24 | 89.5 |
| 3.0 | 36 | 112.0** |
| 10.0 | 23 | 136.0** |
| 30.0 | 13 | 201.0* |

*: significantly different from vehicle, p < 0.05, Mann-Whitney U Test
**: significantly different from vehicle, p < 0.025, Mann-Whitney U Test Utility The foregoing test results suggest that the compounds of this invention have utility in the treatment of cognitive disorders and/or neurological function deficits and/or mood and mental disturbances in patients suffering from nervous system disorders like Alzheimer's disease, Parkinson's disease, senile-dementia, multi-infarct dementia, Huntington's disease, mental retardation, Myasthenia Gravis, etc. Compounds of this invention can be administered to treat said deficiencies by any means that produces contact of the active agent with the agent's site of action in the body of a mammal. The compounds can be administered by any conventional means available for use in conjunction with pharmaceuticals either as individual therapeutic agent or in combination of therapeutic agents. They can be administered alone, but are generally administered with a pharmaceutical carrier selected on the basis of the chosen route of administration and standard pharmaceutical practice.

The dosage administered will vary depending on the use and known factors such as the pharmacodynamic character of the particular agent, and its mode and route of administration; the recipient's age, weight, and health; nature and extent of symptoms; kind of concurrent treatment; frequency of treatment; and the desired effect. For use in the treatment of said diseases or conditions, the compounds of this invention can be orally administered daily at a dosage of the active ingredient of 0.001 to 100 mg/kg of body weight. Ordinarily, a dose of 0.01 to 10 mg/kg/day in divided doses one to four times a day, or in sustained release formulation was effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally in solid dosage forms, such as capsules, tablets, and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar coated or film coated to mask any unpleasant taste, or used to protect the active ingredients from the atmosphere, or to allow selective disintegration of the tablet in the gastrointestinal tract.

Liquid dosage forms for oral administration can contain coloring and flavoring agents to increase patient acceptance.

In general, water, pharmaceutically acceptable oils, saline, aqueous dextrose (glucose), and related sugar solutions and glycols, such as propylene glycol or polyethylene glycol, are suitable carders for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences", A. Osol, a standard reference in this field.

Useful pharmaceutical dosage-forms for administration of the compounds of this invention can be illustrated as follows:

Capsules

A large number of unit capsules are prepared by filling standard two-piece hard gelatin capsules each with 100 mg of powdered active ingredient, 150 mg lactose, 50 mg cellulose, and 6 mg magnesium stearate.

Soft Gelatin Capsules

A mixture of active ingredient in a digestible oil such as soybean, cottonseed oil, or olive oil is prepared and injected by means of a positive displacement was pumped into gelatin to form soft gelatin capsules containing 100 mg of the active ingredient. The capsules are washed and dried.

Tablets

A large number of tablets are prepared by conventional procedures so that the dosage unit was 100 mg of active ingredient, 0.2 mg of colloidal silicon dioxide, 5 mg of magnesium stearate, 275 mg of microcrystalline cellulose, 11 mg of starch, and 98.8 mg lactose. Appropriate comings may be applied to increase palatability or delayed absorption.

The compounds of this invention may also be used as reagents or standards in the biochemical study of neurological function, dysfunction, and/or disease.

What is claimed is:

1. A compound of the formula

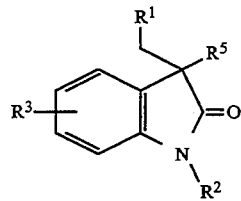

$R^1$ is 4-, 3-, or 2-pyridyl, 2-, or 3-fluoro-4-pyridyl or 3-fluoro-4-pyridyl;

$R^2$ is alkyl of 1 to 10 carbons, cycloalkyl of 3 to 8 carbons, 2-, 3-, or 4-pyridyl, Phe or Phe-W;

Phe is a phenyl group;

W is F, Cl, Br, —OH, $R^4$, —$OR^4$, —$NO_2$, —$NH_2$, —$NHR^4$, —$NR^4R^4$, —CN, —$S(O)_mR^4$;

$R^3$ is H, F, Cl, Br, —CN, —OH, —$NO_2$, —$NH_2$, —$CF_3$, —$NHR^4$, —$NR^4R^4$, $R^4$, —$OR^4$, —$S(O)_mR^4$;

$R^4$ is independently selected at each occurrence from the group: alkyl of 1 to 4 carbons, Phe, and $CH_2$Phe;

$R^5$ is —$(CH_2)_n$—Y or —$OCOR^4$;

Y is $NH_2$, —$NHR^4$, —$NR^4R^4$, —$NHCOR^4$, —$NHCO_2R^4$, F, Cl, Br, $OR^4$, —$S(O)_mR^4$, —$CO_2H$, —$CO_2R^4$, —CN, —$CONR^4R^4$, —$CONHR^4$, —$CONH_2$, —$COR^4$; —CH=$CHCO_2R^4$, $OCOR^4$, —C≡$CCO_2R^4$, —CH=$CHR^4$, or —C≡$CR^4$;

m is 0, 1 or 2;

n is 1 to 7;

and physiologically suitable salts thereof.

2. A compound of claim 1 wherein $R^1$ is selected from the group consisting of 4-pyridyl and 2- fluoro-4-pyridyl.

3. A compound of claim 1 wherein $R^5$ is —$(CH_2)_n$—Y.

4. A compound of claim 3 wherein n is 1 to 5 and Y is selected from the group consisting of —$NH_2$, —$NHR^4$, —$NR^4R^4$, F, Cl, Br, —$CO_2H$, —$CO_2R^4$, —CN, —$CONHR^4$, —$CONH_2$, —$CONR^4R^4$, —$COR^4$, —CH=$CHCO_2R^4$, and —$OCOR^4$.

5. A compound of claim 1, where W is selected from the group consisting of F, Cl, Br, $R^4$, —$OR^4$, —$S(O)_m$—$R^4$, —CN, —$NO_2$, and —$NH_2$.

6. A compound of claim 1 wherein $R^4$ is alkyl of 1to 4 carbons.

7. A compound of claim 2 wherein $R^5$ is —$(CH_2)_n$—Y.

8. A compound of claim 7 where n is 1 to 4; Y is selected from the group consisting of —$CO_2R^4$, —CN, —$CONHR^4$, —CH=$CHCO_2R^4$, and —$OCOR^4$; and $R^4$ is alkyl of 1 to 2 carbon atoms.

9. A compound of claim 1 where $R^2$ is selected from the group consisting of 4-pyridyl, Phe and Phe-W.

10. A compound of claim 9 where W is selected from the group consisting of F, Cl, Br, —$NO_2$, —CN, and —$CH_3$.

11. A compound of claim 1 where $R^3$ is selected from the group consisting of H, F, Cl, and Br.

12. A compound of claim 1 where $R^1$ is selected from the group consisting of 4-pyridyl and 2-fluoro-4-pyridyl;

$R^5$ is —$(CH_2)_n$—Y;

n is 1 to 4;

Y is selected from the group consisting of —$CO_2R^4$, —CN, —$CONHR^4$, —CH=$CHCO^2R^4$, and —$OCOR^4$;

$R^2$ is selected from the group consisting of 4-pyridyl, Phe and Phe-W;

W is selected from the group consisting of F, Cl, Br, $NO_2$, CN, and $CH_3$;

$R^3$ is selected from the group consisting of H, F, Cl, and Br; and $R^4$ is alkyl of 1 to 2 carbons.

13. The compound of claim 1 which is 2,3-Dihydro-2-oxo-1-phenyl-3-(4-pyridinylmethyl)-1H-indole-3-butanoic acid ethyl ester Hydrochloride.

14. The compound of claim 1 which is (+)-2,3-Dihydro-2-oxo-1-phenyl-3-(4-pyridinylmethyl)-1H-indole-3-butanoic acid ethyl ester Hydrochloride.

15. The compound of claim 1 which is 2,3-Dihydro-2-oxo-1-phenyl-3-(4-pyridinylmethyl)-1H-indole-3-pentanenitrile Hydrochloride.

16. The compound of claim 1 which is 2,3-Dihydro-2-oxo-1-phenyl-3-(4-pyridinylmethyl)-1H-indole-3-butanenitrile Hydrochloride.

17. The compound of claim 1 which is 2,3-Dihydro-2-oxo-1-phenyl-3-(4-pyridinylmethyl)-1H-indole-3-hexanenitrile Hydrochloride.

18. A pharmaceutical composition comprising a suitable pharmaceutical carrier and a therapeutically effective amount of a compound of claim 1.

19. A pharmaceutical composition comprising a suitable pharmaceutical carrier and a therapeutically effective amount of a compound of claim 2.

20. A pharmaceutical composition comprising a suitable pharmaceutical carrier and a therapeutically effective amount of a compound of claim 3.

21. A pharmaceutical composition comprising a suitable pharmaceutical carrier and a therapeutically effective amount of a compound of claim 4.

22. A pharmaceutical composition comprising a suitable pharmaceutical carrier and a therapeutically effective amount of a compound of claim 5.

23. A pharmaceutical composition comprising a suitable pharmaceutical carrier and a therapeutically effective amount of a compound of claim 6.

24. A pharmaceutical composition comprising a suitable pharmaceutical carrier and a therapeutically effective amount of a compound of claim 7.

25. A pharmaceutical composition comprising a suitable pharmaceutical carrier and a therapeutically effective amount of a compound of claim 8.

26. A pharmaceutical composition comprising a suitable pharmaceutical carrier and a therapeutically effective amount of a compound of claim 9.

27. A pharmaceutical composition comprising a suitable pharmaceutical carrier and a therapeutically effective amount of a compound of claim 10.

28. A pharmaceutical composition comprising a suitable pharmaceutical carrier and a therapeutically effective amount of a compound of claim 11.

29. A pharmaceutical composition comprising a suitable pharmaceutical carrier and a therapeutically effective amount of a compound of claim 12.

30. A pharmaceutical composition comprising a suitable pharmaceutical carrier and a therapeutically effective amount of a compound of claim 13.

31. A pharmaceutical composition comprising a suitable pharmaceutical carrier and a therapeutically effective amount of a compound of claim 14.

32. A pharmaceutical composition comprising a suitable pharmaceutical carrier and a therapeutically effective amount of a compound of claim 15.

33. A pharmaceutical composition comprising a suitable pharmaceutical carrier and a therapeutically effective amount of a compound of claim 16.

34. A pharmaceutical composition comprising a suitable pharmaceutical carrier and a therapeutically effective amount of a compound of claim 17.

35. A method for the treatment of cognitive or neurological dysfunction in a mammal comprising administering to the mammal a therapeutically effective amount of a compound of claim 1.

36. A method for the treatment of cognitive or neurological dysfunction in a mammal comprising administering to the mammal a therapeutically effective amount of a compound of claim 2.

37. A method for the treatment of cognitive or neurological dysfunction in a mammal comprising administering to the mammal a therapeutically effective amount of a compound of claim 3.

38. A method for the treatment of cognitive or neurological dysfunction in a mammal comprising administering to the mammal a therapeutically effective amount of a compound of claim 4.

39. A method for the treatment of cognitive or neurological dysfunction in a mammal comprising administering to the mammal a therapeutically effective amount of a compound of claim 5.

40. A method for the treatment of cognitive or neurological dysfunction in a mammal comprising administering to the mammal a therapeutically effective amount of a compound of claim 6.

41. A method for the treatment of cognitive or neurological dysfunction in a mammal comprising administering to the mammal a therapeutically effective amount of a compound of claim 7.

42. A method for the treatment of cognitive or neurological dysfunction in a mammal comprising administering to the mammal a therapeutically effective amount of a compound of claim 8.

43. A method for the treatment of cognitive or neurological dysfunction in a mammal comprising administering to the mammal a therapeutically effective amount of a compound of claim 9.

44. A method for the treatment of cognitive or neurological dysfunction in a mammal comprising administering to the mammal a therapeutically effective amount of a compound of claim 10.

45. A method for the treatment of cognitive or neurological dysfunction in a mammal comprising administering to the mammal a therapeutically effective amount of a compound of claim 11.

46. A method for the treatment of cognitive or neurological dysfunction in a mammal comprising administering to the mammal a therapeutically effective amount of a compound of claim 12.

47. A method for the treatment of cognitive or neurological dysfunction in a mammal comprising administering to the mammal a therapeutically effective amount of a compound of claim 13.

48. A method for the treatment of cognitive or neurological dysfunction in a mammal comprising administering to the mammal a therapeutically effective amount of a compound of claim 14.

49. A method for the treatment of cognitive or neurological dysfunction in a mammal comprising administering to the mammal a therapeutically effective amount of a compound of claim 15.

50. A method for the treatment of cognitive or neurological dysfunction in a mammal comprising administering to the mammal a therapeutically effective amount of a compound of claim 16.

51. A method for the treatment of cognitive or neurological dysfunction in a mammal comprising administering to the mammal a therapeutically effective amount of a compound of claim 17.

* * * * *